US011389080B2

(12) United States Patent
Geissler et al.

(10) Patent No.: US 11,389,080 B2
(45) Date of Patent: Jul. 19, 2022

(54) SYSTEM AND METHOD FOR DIAGNOSIS OF BOVINE DISEASES USING AUSCULTATION ANALYSIS

(75) Inventors: Randolph K. Geissler, Hudson, WI (US); Garrett W. Taylor, Oakley, KS (US); Wade A. Taylor, Oakley, KS (US); Thomas H. Noffsinger, Benkelman, NE (US); Steve A. Lewis, Bloomington, MN (US); Scott A. Nelson, Egan, MN (US)

(73) Assignee: INTERVET INC., Madison, NJ (US)

( * ) Notice: Subject to any disclaimer, the term of this patent is extended or adjusted under 35 U.S.C. 154(b) by 1564 days.

(21) Appl. No.: 13/442,569

(22) Filed: Apr. 9, 2012

(65) Prior Publication Data

US 2012/0215077 A1 Aug. 23, 2012

Related U.S. Application Data

(63) Continuation-in-part of application No. 12/267,448, filed on Nov. 7, 2008, now Pat. No. 8,152,734.
(Continued)

(51) Int. Cl.
*A61B 5/08* (2006.01)
*A61B 7/04* (2006.01)
(Continued)

(52) U.S. Cl.
CPC .............. *A61B 5/08* (2013.01); *A61B 7/003* (2013.01); *A61B 7/04* (2013.01); *A61B 5/7257* (2013.01); *A61B 2503/40* (2013.01)

(58) Field of Classification Search
CPC .......... A61B 2503/40; A61B 7/04; A61B 5/08
See application file for complete search history.

(56) References Cited

U.S. PATENT DOCUMENTS 4,109,643 A * 8/1978 Bond ................. A61B 5/02416
356/41
4,720,866 A 1/1988 Elias et al.
(Continued)

FOREIGN PATENT DOCUMENTS

AU 2005/100352 6/2005
CN 2234248 9/1996
(Continued)

OTHER PUBLICATIONS

Chiumello et al. "Mechanical ventilation affects local and systemic cytokines in an animal model of acute respiratory distress syndrome." American Journal of Respiratory and Critical Care Medicine, Jul. 1999, vol. 160, No. 1, pp. 109-116.
(Continued)

*Primary Examiner* — Lynsey C Eiseman
*Assistant Examiner* — Amanda L Steinberg
(74) *Attorney, Agent, or Firm* — Berg Hill Greenleaf Ruscitti LLP

(57) ABSTRACT

A system and method are provided for diagnosis of animal respiratory diseases using auscultation techniques. Animal lung sounds are recorded and digitized. Lung sounds are obtained by an electronic digital stethoscope or a wireless audio digital recording unit. The sounds are stored as digital data, and one or more algorithms are applied to the data for producing an output to the user indicative of the health of the animal. The acoustic characteristics of the sound are compared with baseline data in the algorithms. One embodiment includes a digital stethoscope with an integral display. Another embodiment provides a system for gathering information about an animal to include not only auscultation data, but also information from other field devices such as temperature probes or weigh scales. The combined information can be analyzed by system software to generate detailed
(Continued)

information to a user to include a diagnosis and recommended treatment options.

8 Claims, 13 Drawing Sheets

Related U.S. Application Data

(60) Provisional application No. 60/990,834, filed on Nov. 28, 2007.

(51) Int. Cl.
*A61B 7/00* (2006.01)
*A61B 5/00* (2006.01)

(56) References Cited

U.S. PATENT DOCUMENTS

| | | | |
|---|---|---|---|
| 4,928,705 A | 5/1990 | Sekhar et al. | |
| 5,010,889 A | 4/1991 | Bredesen et al. | |
| 5,025,809 A | 6/1991 | Johnson et al. | |
| 5,165,417 A | 11/1992 | Murphy, Jr. | |
| 5,218,969 A * | 6/1993 | Bredesen | A61B 7/04 381/67 |
| 5,255,685 A | 10/1993 | Parra | |
| 5,301,679 A | 4/1994 | Taylor | |
| 5,769,755 A * | 6/1998 | Henry | A63B 71/0622 116/212 |
| 5,825,895 A * | 10/1998 | Grasfield | A61B 7/04 381/67 |
| 6,053,872 A | 4/2000 | Mohler | |
| 6,210,344 B1 * | 4/2001 | Perin | A61B 7/04 600/528 |
| 6,261,238 B1 | 7/2001 | Gavriely | |
| 6,287,254 B1 | 9/2001 | Dodds | |
| 6,309,352 B1 | 10/2001 | Oraevsky et al. | |
| 6,394,967 B1 | 5/2002 | Murphy, Jr. | |
| 6,396,931 B1 | 5/2002 | Malilay | |
| 6,418,876 B1 | 7/2002 | Hall et al. | |
| 6,443,907 B1 | 9/2002 | Mansy et al. | |
| 6,520,924 B2 | 2/2003 | Lee | |
| 6,535,131 B1 | 3/2003 | Bar-Shalom et al. | |
| 6,706,002 B1 | 3/2004 | Halleck et al. | |
| 6,887,208 B2 | 5/2005 | Kushnir et al. | |
| 6,949,075 B2 | 9/2005 | Hatlesad et al. | |
| 6,953,436 B2 | 10/2005 | Watrous et al. | |
| 6,966,400 B1 | 11/2005 | Rollins et al. | |
| 6,979,298 B2 | 12/2005 | Vodyanoy et al. | |
| 7,026,941 B1 | 4/2006 | Anderson | |
| 7,066,894 B2 | 6/2006 | Halleck et al. | |
| 7,346,174 B1 * | 3/2008 | Smith | A61B 7/026 181/131 |
| 7,642,730 B2 * | 1/2010 | Dowling | H05B 37/02 315/292 |
| 8,152,734 B2 | 4/2012 | Noffsinger et al. | |
| 8,790,270 B2 * | 7/2014 | Landesberg | A61B 5/062 600/529 |
| 2002/0010390 A1 | 1/2002 | Guice et al. | |
| 2002/0188227 A1 * | 12/2002 | Chong | A61B 7/04 600/586 |
| 2003/0002685 A1 * | 1/2003 | Werblud | A61B 7/04 381/67 |
| 2003/0072457 A1 * | 4/2003 | Grasfield | A61B 7/04 381/67 |
| 2004/0092846 A1 * | 5/2004 | Watrous | A61B 7/04 600/586 |
| 2004/0260188 A1 * | 12/2004 | Syed | A61B 5/0456 600/509 |
| 2005/0014999 A1 | 1/2005 | Rahe-Meyer | |
| 2005/0090755 A1 * | 4/2005 | Guion | A61B 7/00 600/528 |
| 2005/0137464 A1 | 6/2005 | Bomba | |
| 2005/0143628 A1 | 6/2005 | Dai et al. | |
| 2005/0257748 A1 | 11/2005 | Kriesel et al. | |
| 2006/0198533 A1 | 9/2006 | Wang et al. | |
| 2006/0227979 A1 * | 10/2006 | Chen | A61B 7/04 381/67 |
| 2006/0253005 A1 | 11/2006 | Drinan | |
| 2007/0055151 A1 * | 3/2007 | Shertukde | A61B 5/02007 600/437 |
| 2007/0088194 A1 | 4/2007 | Tahar et al. | |
| 2007/0282174 A1 * | 12/2007 | Sabatino | A61B 5/7257 600/300 |
| 2008/0013747 A1 * | 1/2008 | Tran | A61B 5/0452 381/67 |
| 2008/0037800 A1 * | 2/2008 | Grasfield | A61B 7/04 381/67 |
| 2008/0071155 A1 * | 3/2008 | Kiani | A61B 5/02416 600/324 |
| 2008/0232605 A1 | 9/2008 | Bagha | |
| 2008/0269625 A1 * | 10/2008 | Halperin | A61B 5/08 600/508 |
| 2009/0012415 A1 * | 1/2009 | Thiagarajan | A61B 5/0006 600/528 |
| 2009/0209849 A1 | 8/2009 | Rowe et al. | |
| 2010/0056956 A1 * | 3/2010 | Dufresne | A61B 7/04 600/586 |
| 2010/0145210 A1 | 6/2010 | Graff et al. | |
| 2010/0160809 A1 | 6/2010 | Laurence et al. | |
| 2010/0286532 A1 | 11/2010 | Farringdon et al. | |
| 2012/0040381 A1 | 2/2012 | Snider et al. | |
| 2012/0115808 A1 | 5/2012 | Della Valle et al. | |

FOREIGN PATENT DOCUMENTS

| | | |
|---|---|---|
| CN | 2567709 | 8/2003 |
| EP | 0956821 | 11/1999 |
| WO | WO 2011/120524 | 10/2011 |
| WO | WO 2013/006066 | 1/2013 |

OTHER PUBLICATIONS

International Search Report and Written Opinion for International (PCT) Patent Application No. PCT/US14/13486, dated Apr. 21, 2014 12 pages.
International Preliminary Report on Patentability for International (PCT) Patent Application No. PCT/US2014/013486, dated Aug. 20, 2015 11 pages.
Extended Search Report for European Patent Application No. 09825178.8, dated May 28, 2013 6 pages.
U.S. Appl. No. 13/760,968, filed Feb. 6, 2013, Brattain et al.
International Search Report and Written Opinion for International (PCT) Patent Application No. PCT/US13/23044, dated Apr. 12, 2013 9 pages.
International Preliminary Report on Patentability for International (PCT) Patent Application No. PCT/US2013/023044, dated Dec. 18, 2014 8 pages.
International Search Report for International (PCT) Patent Application No. PCT/US2009/060080, dated Dec. 3, 2009.
Written Opinion for International (PCT) Patent Application No. PCT/US2009/060080, dated Dec. 3, 2009.
International Preliminary Report on Patentability for International Patent Application No. PCT/US2009/060080, dated May 19, 2011 8 pages.
"Auscultation", Wikipedia, available at http://en.wikipedia.org/wiki/Auscultation, accessed Nov. 13, 2007, pp. 1-2.
"Fourier Transform", Wikipedia, available at http://en.wikipedia.org/wiki/Fourier_transform, accessed Nov. 9, 2007, pp. 1-14.
"Stethoscope", Wikipedia, available at http://en.wikipedia.org/wiki/Electronic_stethoscope, accessed Nov. 13, 2007, pp. 1-3.
"WAV", Wikipedia, available at http://en.wikipedia.org/wiki/WAV, accessed Nov. 9, 2007, pp. 1-3.
"WAVE File Format", available at http://www.borg.com/~jglatt/tech/wave.htm, accessed Nov. 9, 2007, pp. 1-10.
Car et al., "The Role of leucocytes in the pathogenesis of Fibrin Deposition in Bovine Acute Lung Injury", Am J Path 138 (5):1191-1198, 1991.

(56) References Cited

OTHER PUBLICATIONS

Ferrari et al. "Cough sound description in relation to respiratory diseases in dairy calves." Preventative Veterinary Medicine, Sep. 2010, vol. 96, No. 3-4, pp. 276-280.
Noffsinger, "Lung Auscultation and Sick Calf Management", date unknown, pp. 1-68.
Robinson et al., "Physiology of the Bovine Lung," Departments of Physiology and Large Animal Clinical Sciences, Michigan State University, pp. 192-222, date unknown.
Robinson, "Some functional Consequences of species differences in lung anatomy", Advances in Veterinary Science and Comparative Medicine, vol. 26, pp. 1-33.
Thomson, "The pathogenesis and Lesions of Pneumonia in Cattle", Compendium Cont Ed Pract Vet 7(11): s403-S411,1981.
Veit et al., "The Anatomy and Physiology of Bovine Resp System relating to Pulmonary Disease" Cornell Vet 68:555-581 1978.
Weekley et al., "Potential Morphologic and Physiologic factors that predispose the Bovine Lung to Resp Disease", Compendium Contin Education Pract Vet 17(7):974-982,1995.
"3M™ Littmann® Electronic Stethoscope Model 3100, Hunter Green Tube, 27 inch, 3100HG," 3M, 2012, found at www.3m.com/product/information/Littmann-3100-Electronic-Stethoscope.html, 2 pages.
Dedonder et al. "Lung Auscultation and Rectal Temperature as a Predictor of Lung Lesions and Bovine Respiratory Disease Treatment Outcome in Feedyard Cattle," Bovine Practitioner, 2010, vol. 44, No. 2, pp. 146-153.
Godinho et al. "Efficacy of tulathromycin in the treatment and prevention of natural outbreaks of bovine respiratory disease in European cattle," Veterinary Therapeutics, 2005, vol. 6, No. 2, pp. 122-135.
Harland et al. "Efficacy of parenteral antibiotics for disease prophylaxis in feedlot calves." The Canadian Veterinary Journal, Mar. 1991, vol. 32, No. 3, pp. 163-168.
Hibbard et al. "Dose determination and confirmation of a long-acting formulation of ceftiofur (ceftiofur crystalline free acid) administered subcutaneously for the treatment of bovine respiratory disease," Jorunal of Veterinary Pharmacology and Therapeutics, 2002, vol. 25, No. 3, pp. 175-180.
Loneragan et al. "Trends in mortality ratios among cattle in US feedlots," Journal of the American Veterinary Medical Association, Oct. 2001, vol. 219, No. 8, pp. 1122-1127.
Rerat et al. "Bovine respiratory disease: Efficacy of different prophylactic treatments in veal calves and antimicrobial resistance of isolated Pasteurellaceae," Preventitive Veterinary Medicine, 2012, vol. 103, No. 4, pp. 265-273.
Extended Search Report for European Patent Application No. 13775692.0, dated May 27, 2016 10 pages.
Extended Search Report for European Patent Application No. 14749175.7, dated Oct. 14, 2016 8 pages.
Examination Report in Canadian Application No. 2,867,619 dated Apr. 25, 2019, 4 pages.

\* cited by examiner

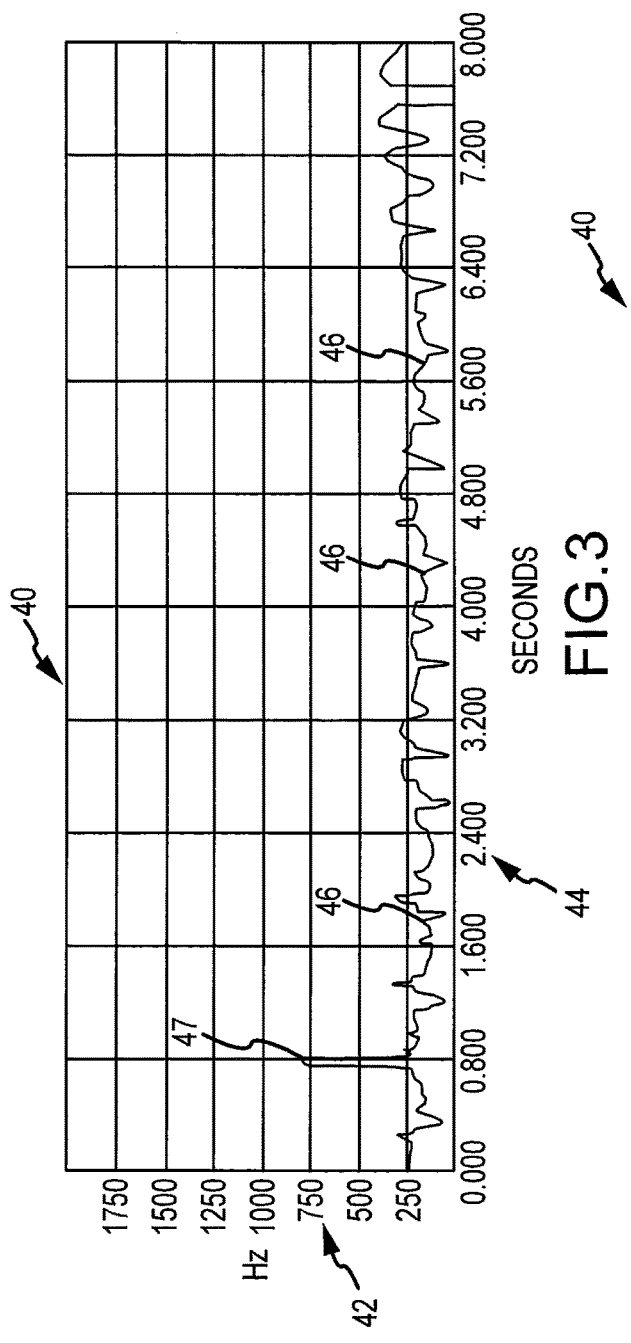
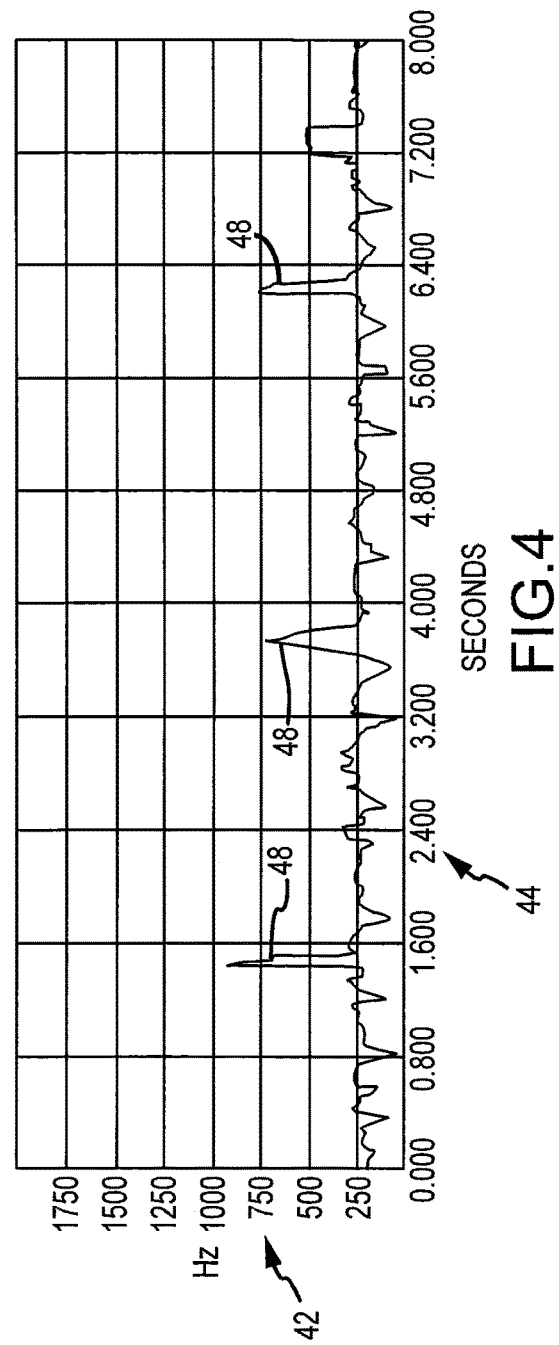
FIG.3
FIG.4

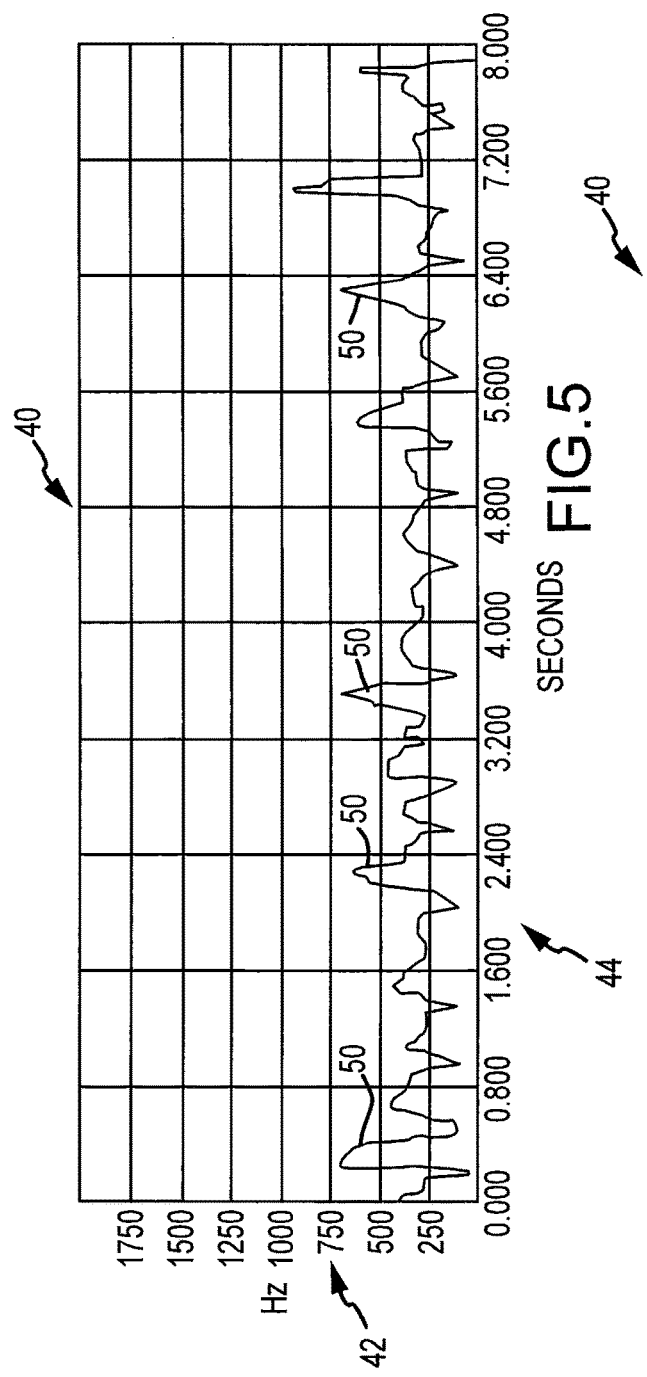
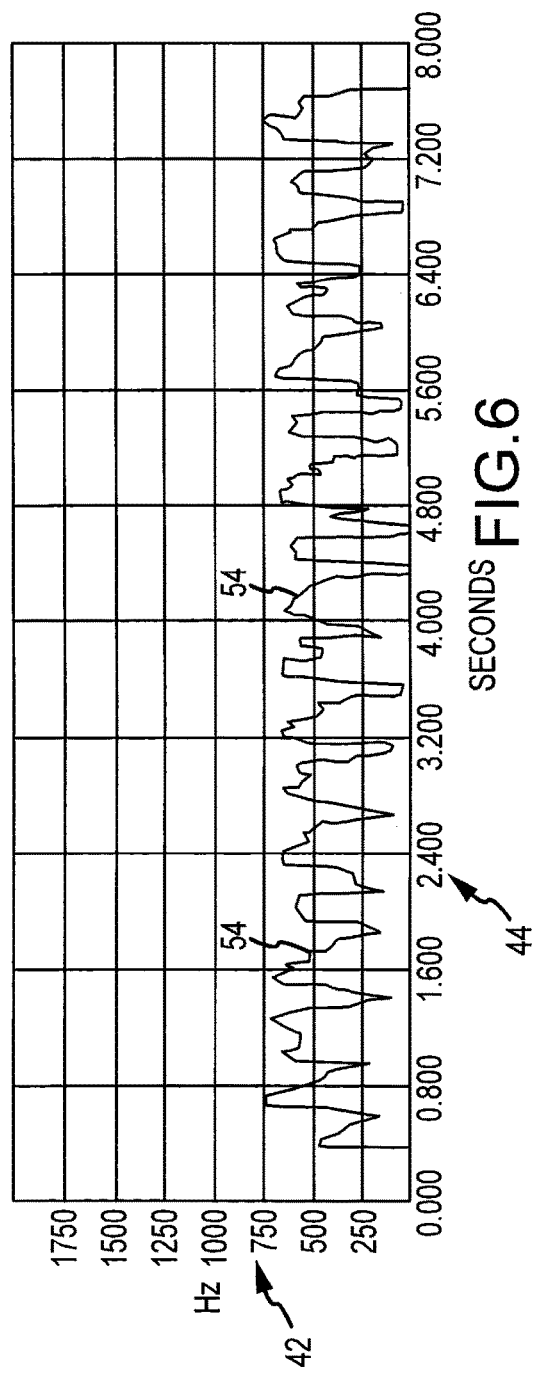

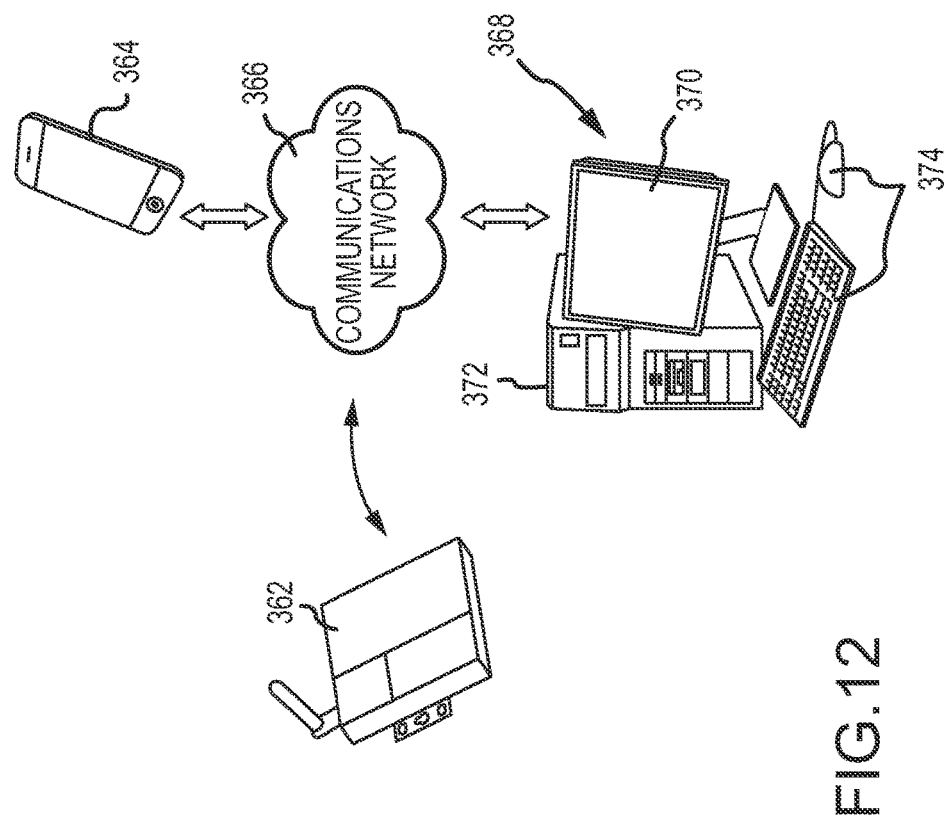
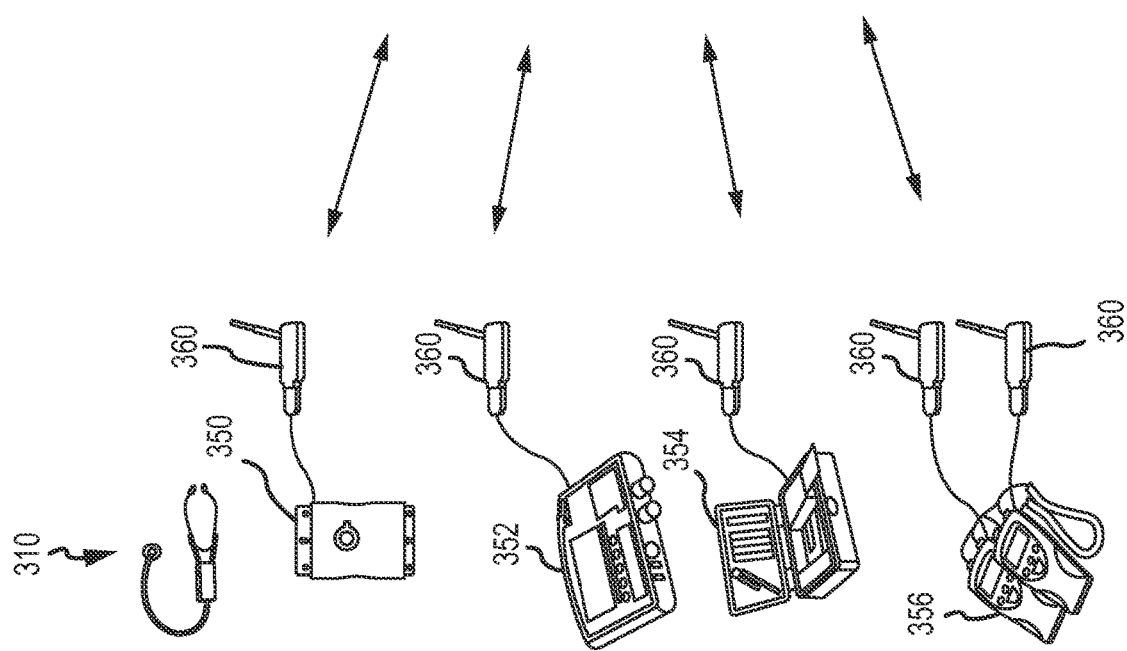
FIG. 12

SYSTEM AND METHOD FOR DIAGNOSIS OF BOVINE DISEASES USING AUSCULTATION ANALYSIS

CROSS REFERENCE TO RELATED APPLICATION

This application is a continuation in part of U.S. patent application Ser. No. 12/267,448 filed on Nov. 7, 2008, which claims priority from U.S. Provisional Patent Applicant No. 60/990,834 filed Nov. 28, 2007, both of which are incorporated by reference herein in their entirety.

FIELD OF THE INVENTION

The present invention generally relates to non-invasive diagnosis of diseases for animals, and more particularly, to a system and method for diagnosis of bovine respiratory diseases using auscultation techniques. The acoustic characteristics of recorded sounds are placed in a digital data format, and then are manipulated in one or more mathematical operations including an algorithm to generate a numerical lung score. The lung scores are compared to existing data that indicate the level of disease in the observed animal. Diagnosis, prognosis, and treatment recommendations can also be generated based upon the lung scores. Embodiments are also provided for electronic digital stethoscopes having integral display units that provide a user an indication of the health of the animal being examined.

BACKGROUND OF THE INVENTION

Cardiovascular diseases, respiratory diseases, and gastrointestinal diseases have been distinguished according to sounds auscultated from the body of a patient. Based upon measurements taken of the different sounds, medical practitioners have been able to diagnose diseases and proceed with treatments.

In order to make a precise diagnosis of an ailment based upon auscultated sounds, extensive empirical knowledge of various and diverse forms of auscultated sounds is necessary. Until recently, auscultation was more art than science since making a diagnosis was based mainly upon the trained ear of a caregiver and not based upon measured data from recorded sounds.

With the advent of digital/electronic stethoscopes, auscultated sounds can be recorded in digital form, and software programs can then manipulate the data in order to analyze characteristics of the data. From this analysis, more precise diagnoses can be made based upon objective criteria and not just upon the trained ear of the attending caregiver.

It is well known to measure auscultated sounds from humans in order to make diagnoses of perceived ailments. However, auscultation for animals such as cattle is used infrequently. There have been very few efforts made to gather data for auscultated bovine sounds for purposes of making conclusions as to the type of disease that may be occurring in bovine species.

Particularly in a feed yard where it is necessary for cattle to be maintained at an optimum state of health for the necessary weight gain to occur, it is critical that sick cattle be identified early for effective treatment and to contribute to biosecurity. The true state of health for cattle can be difficult to measure using traditional techniques such as observation of symptoms to include temperature, posture and visual signs (e.g. nasal discharge, depression, and abdominal fill.). Case definitions for Bovine Respiratory Disease have traditionally included an objective minimal rectal temperature and a subjective clinical score. Clinical trials indicate that objective lung scores provide stronger correlations than rectal temperatures to ultimate case fatality rates, retreatment rates, and treatment costs. Cattle are visually evaluated when they first arrive at the feed yard, and adrenalin associated with handling can often mask disease symptoms. Stethoscopic evaluation of bovine lung sounds can be used to evaluate the oxygen metabolism potential of cattle during various stages of arrival processing. However, because of the lack of current data in objectively categorizing bovine lung sounds, there is a need for developing an automated system and method that can assist a caregiver in assessing these lung sounds and making timely diagnoses.

Bovine respiratory disease is complex and is particularly difficult to treat and diagnose compared to respiratory diseases in humans. The thick musculature that surrounds the thorax of cattle, the heavy hide and possible layers of fat, and the breadth of the ribs complicates the use of a stethoscope to obtain sounds that can be analyzed for purposes of making a diagnosis.

Because of problems associated with effectively gathering auscultated sounds from cattle, and the general lack of knowledge as to how to analyze these sounds, the cattle industry has been slow in developing automated diagnostic processes that can effectively use auscultated data.

One patent reference that discusses the use of acoustics for detection of respiratory conditions is the U.S. Pat. No. 6,443,907. This reference specifically discloses diagnostic techniques to enable detection of respiratory conditions within a patient's body. Data gathered from auscultation is compared to reference acoustic characteristics and/or predetermined threshold values to determine if an abnormal respiratory condition is present within the patient. The diagnostic technique includes the processing of acoustic data by calculating energy ratios using energy values within high and low frequency bands, signal time delays, and/or dominant frequencies; the calculated values are then compared to predetermined reference thresholds to generate outputs indicative of the respiratory condition within the patient.

The U.S. Pat. No. 6,520,924 discloses an automatic diagnostic apparatus using a digital stethoscope. The diagnosis is determined based upon a comparison of recorded auscultated sounds versus standard data of auscultated sounds for cardiovascular, respiratory, and gastrointestinal diseases. Objective criteria are used to compare the collected auscultated sounds and the standard data to enable a medical practitioner to diagnose a particular disease.

Although auscultation has been well developed for human treatment, there is clearly a need for an automated process and method that can diagnose bovine respiratory diseases.

SUMMARY OF THE INVENTION

In accordance with the present invention, a system and method are provided for diagnosing respiratory diseases of bovine species. Stethoscopic evaluation of bovine lung sounds is used to gather data on the sounds. Collection of lung sounds is preferably obtained by a digital/electronic stethoscope that is capable of expressing sounds in the form of a spectrogram. Collected digital data from the stethoscope is manipulated by computer software that allows real time analysis of the spectrogram and the diagnosis of an ailment based upon numerical lung scores that generally categorize the health of the animal. The lung scores are compared with threshold levels that generally describe the health of the animal and can be further interpreted to correspond to a certain level of disease in the animal. This comparison may also be used to generate one or more recommended treatments. The assigning of numerical lung scores to evaluated cattle is an efficient predictor of respiratory problems.

Through extensive data gathering, it has been found that auscultated sounds from bovine species that fall within particular frequency ranges provide an indication of respiratory disease. Assuming that the stethoscope is placed at the proper location to collect auscultated sounds, collected sounds falling within these frequencies are converted through a series of mathematical operations including one or more algorithms to produce the numerical lung scores. These lung scores then correspond to various levels of respiratory disease and, accordingly, diagnosis, prognosis, and treatment can then be pursued based upon the specific lung scores obtained.

More specifically, it has been determined through testing that auscultated sounds in a range between 500-900 Hz can be used to generate the numerical lung scores and therefore indicate various levels of respiratory disease.

In accordance with the method of the present invention, the auscultated sounds are collected from bovine species by use of a digital stethoscope that is placed approximately three inches above the right elbow of the animal, thereby placing the stethoscope over the right apical lobe. Sounds can also be gathered on the left side approximately three inches above the left elbow, thereby placing the stethoscope over the cardiac lobe. Once the sounds have been gathered and recorded by the digital stethoscope, the data is downloaded to a computing device. The recorded sound is preferably loaded as a .wav file. If another file format is used, in accordance with the present invention, the software is adapted to convert to the .wav format for processing. A .wav file is an industry standard waveform audio format that is used for storing audio on devices such as personal computers. This file is a variant of the RIFF bit-stream format method for storing data in groups, and is presently the main format used on Windows systems for raw audio data. The data recorded from the sound is stored in an array in its raw or basic format. A short-time Fourier transform (STFT) is performed on the raw data with a selected window size of approximately 512 data points and an approximate 50% overlap. The window size refers to the amount of data that each Fourier transform will cover. Each window is overlapped with approximately 50% of the previous window to help improve frequency resolution. Because a Fourier transform functions only with an infinite stationary signal, the dynamic signals recorded have to be separated into many small pieces so that each piece can represent a stationary value at that time. The window size selected has an effect on how accurate of a frequency representation the transform outputs, and a window size of approximately 512 data points has been shown to provide the requisite accuracy for purposes of generating lung scores in accordance with the present invention. For example, sounds sampled at 4000 Hz by a particular type of digital stethoscope could contain 8192 raw data points for every second of recorded sound. The STFT will take the first 512 of these data points and operate on them. The second sweep, because of the overlap, will start at the 256th data point and progress to the 767th data point. This combination of window size and overlap has been shown to provide a good trade off between frequency resolution and time resolution.

Through testing, it has been found that the specific windowing function may include a Hamming function. As understood by those skilled in the art, a Hamming function zeroes the data outside of a specified interval. Windowing functions are used in short time Fourier transforms (STFT) to help combat the problem of spectral leakage. The Hamming function has been shown to help create better frequency resolution, such that the frequencies contained in the recorded sound can be more accurately represented.

The resulting data from each Fourier transform is plotted on a graph to form data points for a spectrogram. In accordance with the present invention, the plotted data creates a spectrogram that is a visual representation of the recorded sounds in the frequency domain where the plotted axes are time and frequency. Amplitudes of frequencies between about 500-900 Hz are the most important in terms of differentiating between varying categories of sounds corresponding to various levels of respiratory disease. The data is then separated into ten primary sets or bands, namely, amplitudes between 500-540 Hz, 540-580 Hz, 580-620 Hz, 620-660 Hz, 660-700 Hz, 700-740 Hz, 740-780 Hz, 780-820 Hz, 820-860 Hz, 860-900 Hz.

Each frequency band is trimmed to remove the first and last portion of the recorded sound. The trimming function can be achieved through the use of a user selection screen in a computer software program that generates a spectrogram of the recorded sound. The user can manually trim the applicable first and last portion of the recorded sound by viewing the recorded sound in the spectrogram and using the prescribed software function to remove the desired portions of the recorded sound. The user also evaluates the recorded sound as a whole in order that only the pertinent sections of each recorded sound are selected for analysis, thereby ensuring that any unnecessary data is not included. For example, with the use of some stethoscopes, when the stethoscope is first placed on an animal, a significant popping sound may be recorded. This popping sound is easily removable by the user deleting or removing the portion of the spectrogram that corresponds to the popping sound in the user selection screen. The resulting frequencies obtained may be referred to as trimmed frequencies. Each of the ten trimmed frequency bands is then fed to a finite impulse response (FIR) filter, such as a 125 tap FIR filter with identical coefficients. For purposes of this calculation, auscultated sounds over a period of three full respirations of the animal are adequate for effective scoring. In order to account for differences in the respiration rates of animals and any noise that may be present, it has been found that recording sounds over an 8 second period of time is adequate. This time frame however can be modified to account for any unusual circumstances at the time of auscultation.

The numerical results of applying each FIR filter is then used to formulate a calculated numerical lung score that is compared to established baseline data for establishing a presumptive diagnosis of disease severity.

The formula or equation for establishing lung scores can therefore be expressed as follows where the X values are the numerical result of applying the FIR filter in the stated frequency range:

$x_1$=result of 500-540 Hz FIR filter; $x_2$=result of 540-580 Hz FIR filter;

$x_3$=result of 530-620 Hz FIR filter; $x_4$=result of 620-660 Hz FIR filter;

$x_5$=result of 660-700 Hz FIR filter; $x_6$=result of 700-740 Hz FIR filter;

$x_6$=result of 700-740 Hz FIR filter; $x_7$=result of 740-730 Hz FIR filter;

$x_8$=result of 730-820 Hz FIR filter; $x_9$=result of 320-860 Hz FIR filter;

$x_{10}$=result of 360-900 Hz FIR filter;

$$\text{score} = 0.205x_1 + 0.075x_2 + 0.02x_3 + 0.2x_4 + 0.35x_5 + 0.02x_6 + 0.02x_7 + 0.09x_8 + 0.01x_9 + 0.01x_{10}$$

The coefficients in the lung score equation were determined by gathering data on a large number of sounds, and comparing the sounds to determine if a numerical relationship could be established that correlated the results of applying the FIR filter to sounds in the various frequency ranges with a presumptive diagnosis. The coefficients were established in such a way that the lung scores could be calculated in an increasing order from healthiest (smallest) to sickest (largest), and such that the lung score categories could be easily divided to correspond to various discrete diagnoses. From this exhaustive data gathering and mathematical development exercise, the lung score equation was derived.

Once a calculated lung score is obtained, it is compared to baseline data in the form of threshold values that generally correspond to bovine respiratory conditions. These threshold values have been established as a result of a number of tests in which the threshold values consistently show a direct relationship with the state of health of the animal being evaluated. The threshold values can be expressed in terms of a Scaled Lung Score between 1 and 9. These Scaled Lung Scores may be easier for the caregiver to record and report as opposed to the actual calculated lung scores. As listed below, a bovine respiratory condition is indicated as a function of a range of calculated lung scores and a corresponding Scaled Lung Score. Thus, the range of calculated lung scores as they correspond to respiratory conditions and the Scaled Lung Scores are as follows:

a. Scaled Lung Score 1 (Low Normal)=calculated lung score between 0-74.5
b. Scaled Lung Score 2 (High Normal)=calculated lung score between 74.5-149
c. Scaled Lung Score 3 (Low Mild acute)=calculated lung score between 150-165
d. Scaled Lung Score 4 (High Mild acute)=calculated lung score between 165-180
e. Scaled Lung Score 5 (Low Severe acute)=calculated lung score between 181-250.5
f. Scaled Lung Score 6 (High Severe acute):=calculated lung score between 250.5-320
g. Scaled Lung Score 7 (Low Chronic)=calculated lung score between 320-400
h. Scaled Lung Score 8 (Median Chronic)=calculated lung score between 400-500
i. Scaled Lung Score 9 (High Chronic)=calculated lung score between 500 and above Calculated lung scores that fall close to or above these threshold levels of the Scaled Lung Scores indicate presumptive diagnosis of the corresponding conditions.

For example, a calculated lung score of 175 would indicate a diagnosis of a high mild acute respiratory condition (Scaled Lung Score 4) and approaching a severe acute condition (Scaled Lung Score 5). A calculated lung score of 425 would indicate a median chronic condition (Scaled Lung Score 8), and one that represents disease of longer duration accompanied by some irreversible lung consolidation. Although the calculated lung scores are provided in distinct ranges, it shall be understood that calculated lung scores that fall close to the end of one range and the beginning of the next range may be worthy of further analysis by the caregiver to ensure the assignment of the lung score is consistent with other symptoms exhibited by the animal. Thus, the general ranges are an excellent indicators of lung conditions, but some lung scores may be worthy of additional analysis.

Additional filtering techniques may be used to improve analysis of the recorded sounds. Three additional filters that can be used to eliminate interfering sounds include a heartbeat reduction filter, an adaptive bandstop filter, and a pop/crackle filter. The heartbeat filter is based on an adaptive threshold piece wise interpolation technique that is used to eliminate the noise associated with the heartbeat and that can otherwise interfere with recorded lung sounds. The adaptive bandstop filter is based on the same technique as the heartbeat filter, but is instead focused on eliminating any interference noise emitted at a constant frequency throughout the recorded sound, such as the noise generated by a cattle chute. The pop/crackle filter is used to eliminate any remaining pops or crackles associated with stethoscope movement that remain on the user selection screen.

In accordance with basic functioning of the software of the present invention, a user can select a particular file that corresponds to recorded sound data for a particular animal taken at a particular time. This file can include other identifying information such as the location where the sound was recorded, how it was recorded (e.g., chute side and type of stethoscope used). Once the user has selected the particular file, a spectrogram of the sound along with the score for that sound is shown on a user interface. The spectrogram may include the use of various colors that indicate the amplitudes of the frequencies recorded. Also in accordance with the present invention, the numerical values of the lung scores can each correspond to one or more diagnoses taken from a database of diagnoses, a database of recommended treatment(s) for each diagnosis, and prognoses for improvement based on the diagnoses and recommended treatment(s). Accordingly, the user interface may also display the diagnoses, recommended treatments, and prognoses. The recommended treatments and prognoses will be generated from the calculated lung scores and other factors such as age, weight, days on feed, projected market date, season, origin history, risk category, and rectal temperature.

Also, the spectrograms assist a caregiver in further analyzing the particular pathology associated with the animal since there may be other indications within the spectrogram that assist the caregiver in making a diagnosis. For example, comparing the amplitudes of the recorded sounds during inhalation and exhalation can also be an indicator as to a particular respiratory condition.

With respect to a preferred device for capturing auscultated sounds from the bovine species, a preferred device would include a stethoscope incorporated within a chest piece that communicates either wired or wirelessly with a portable LCD touch screen that displays the spectrogram/waveform of the recorded sound. The portable LCD touch screen could be, for example, a personal digital assistant (PDA) that contains the necessary software to generate a screen display with the spectrogram of the recorded sounds. As discussed below, it is contemplated within the present invention that the user has the option of filtering extraneous data from the recorded wave forms so that the wave forms reflect accurate data corresponding to the actual sound emitted from the animal.

In another embodiment of the invention, an electronic digital stethoscope is provided with an integral display that enables a user to view the lung score directly on the device or to view some other visual indication of the state of the animal's health. In one aspect of this embodiment, it is contemplated that the stethoscope has a wireless capability to communicate wirelessly with a remote computer. The computer receives a digitized lung sound from the stethoscope. A selected algorithm is applied to this digitized data on the computer, and a lung score or some other tangible output is produced that provides an indication of the animal's health. This output is then sent wirelessly back to the stethoscope for display for the user. In another aspect of this embodiment, it is contemplated that the digital stethoscope itself may incorporate a microprocessor, associated memory, and software or firmware that is capable of generating the lung score or some other output indicative of the health of the animal. Thus, the sounds recorded by the stethoscope are manipulated by the microprocessor to generate the lung score output or another output indicating the animal health, and a remote computer is not necessary.

In lieu of generating a lung score, other indications or outputs that can be generated for the user may include a message or report that summarizes the perceived health of the animal as judged by the algorithm(s) applied to the recorded lung sounds. For example, a message can be produced on the integral display of the device that lists the health condition of the animal (e.g., mild acute, acute, etc.), along with a recommendation for treatment such as a dosage of medication. It is also contemplated that the health history of the animal can be considered with the generated lung score/recommendation so that if a medication is recommended, it takes into consideration prior medications received, if any, or other conditions of the animal that may prevent or limit the animal from being prescribed medications at that time. Thus, each individual animal would be first identified by the animal's tag, and the recorded sounds would be added to a data file on the remote computer and/or the integral microprocessor memory. After generation of the lung score or health output, the message generated for the user would first take into consideration other recorded factors such as the health history of the animal which may affect the recommended treatment.

In another embodiment of the present invention, a system is provided in which a number of other field devices are capable of communicating with the stethoscope and with the remote computing device for gathering extensive data regarding the animal and for providing predictive health observations to a caregiver. For example, other field devices that could be associated with the sound data recorded by the stethoscope include weigh scales, temperature probes, RFID readers, and other diagnostic equipment. In this system, it is contemplated that wireless communication takes place between each of the field devices and a designated remote computer. Once the electronic digital stethoscope is activated for obtaining lung sounds from an animal, the stethoscope queries or searches for other field devices that have been used to record information about the animal being examined. If there is a field device(s) present that has been used to obtain other information on the animal, data from each of these field devices and the stethoscope are sent wirelessly to the remote computer. This comprehensive and integrated data can therefore be recorded together for immediate use by the user in which the remote computer or other selected display devices such as personal digital assistant can be used to display the integrated data to include a lung score, a health report, or some other tangible indications of the health of the animal.

In yet another embodiment of the present invention, a wireless audio digital recording unit is provided that has the same functionality as the digital stethoscopes described above, but this recording unit provides a convenient means to record sounds through the use of a multi channel microphone in the form of a curved paddle shaped device. More specifically, the recording unit includes a conforming curve shaped recording paddle that is shaped to generally match the curvature of the chest area of the particular animal in which the device is to be used. The recording paddle can be secured to a pole extension that is held by the user enabling the user to be positioned at a further distance from the animal as compared to use of a traditional stethoscope. In the case of livestock held for examination in a cattle chute or some other confined space, caregivers with traditional stethoscopes are required to reach into the chute to place the stethoscope against the animal. It is well known that movement of the animal within the cage can seriously injure the caregiver who may have an appendage that gets trapped within the cage.

Although embodiments of the invention are directed to auscultation analysis for bovine species, the invention is equally applicable to other animal species to include, without limitation, swine, sheep, horses, dogs and cats. Algorithms can be generated for each species to determine threshold values that correspond to the health status of the animal.

Various other features and advantages of the present invention will become apparent from a review of the following detailed description, taken in conjunction with the drawings.

BRIEF DESCRIPTION OF THE DRAWINGS

FIG. 3 is an example spectrogram showing normal lung sounds for bovine specie;

FIG. 4 is another spectrogram illustrating bovine lung sounds, categorized as mild acute;

FIG. 5 is another spectrogram illustrating bovine lung sounds, categorized as severe acute;

FIG. 6 is another spectrogram illustrating bovine lung sounds, categorized as chronic.

FIG. 12 is a system diagram for yet another embodiment of the present invention that provides interconnectivity between various field devices and the digital stethoscope in order to gather a wide range of data simultaneously enabling comprehensive information to be made available for immediate use by a caregiver;

DETAILED DESCRIPTION

Figure 1:
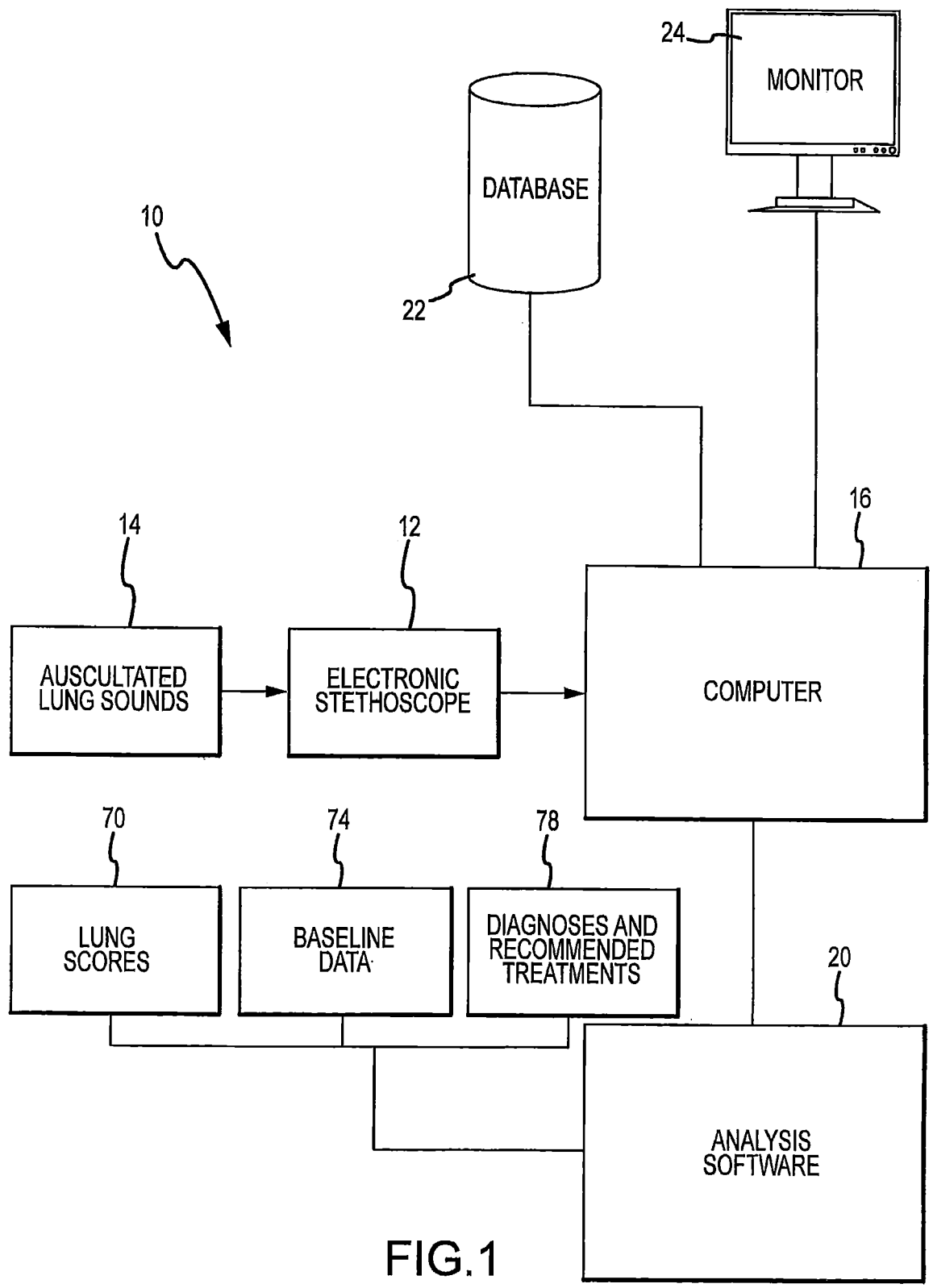
FIG. 1 is a schematic view of the system of the present invention.

Referring to FIG. 1, the system 10 of the present invention is illustrated. An electronic stethoscope 12 is used to gather lung sounds 14 from the animal. The stethoscope 12 detects the sounds, and the sounds are then downloaded in digital form to a computing device 16. The computing device 16 can take a number of forms, such as a standalone personal computer, a portable computing device such as a personal digital assistant (PDA) The computing device 16 includes a conventional microprocessor for manipulation of computer-coded instructions in the form of the analysis software 20. One or more databases 22 accessible by the computing device stores the digital sounds. A user interface such as a monitor 24 allows the user to view the gathered data, to include a spectrogram that may be generated by the analysis software 20 indicative of various attributes of the recorded sound to include frequencies, amplitudes, and other attributes that are recorded over time.

Figure 2:
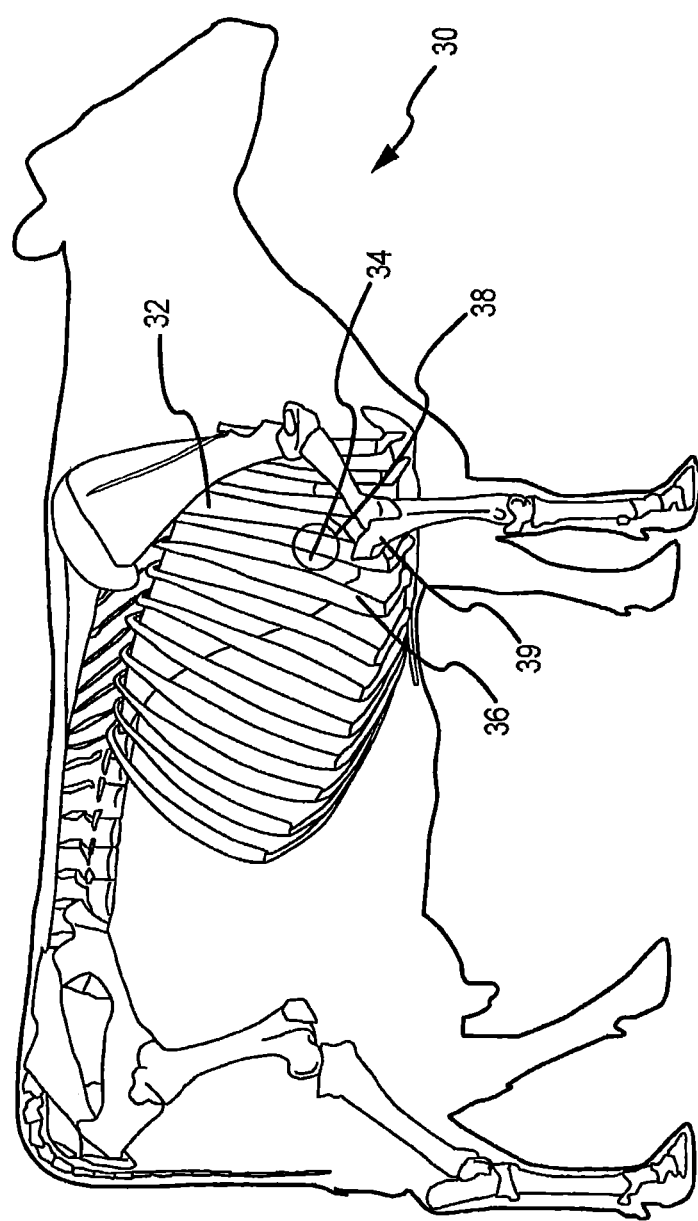
FIG. 2 is a schematic diagram of a bovine specie showing a preferred location where auscultated sounds are gathered, such as by an electronic stethoscope.

The auscultated lung sounds 14 are obtained from the animal in accordance with placement of the stethoscope at designated locations on the animal. Referring now to FIG. 2, a bovine 30 is illustrated with the lungs 32 located at a central region of the body. In this figure, the apical lobe 34 is the preferred location where the sensing device of the stethoscope is placed. As shown, the apical lobe 34 is covered partially by the fourth rib 36. The circle 38 illustrates the preferred location where the stethoscope should be placed, which is approximately three inches above the right elbow 39. With respect to placement of the digital stethoscope, the area 38 has been shown to be an optimum area for data gathering. The Bovine species possesses an extra lobe in their lungs compared to other animals such as humans, referred to as the right apical lobe ventilated by the most anterior accessory tracheal bronchi, making the apical lobe most susceptible to acute aerogenous pneumonia. If auscultated sounds are to be gathered from the left side of the animal, then the preferred location for placement of the stethoscope is approximately the same, i.e., three inches above the left elbow that results in placement of the stethoscope over the cardiac lobe. However on the left side, positioning the stethoscope between the fourth and fifth ribs may provide a better position for gathering the sound. Given that bovines stand on all fours, respiratory disease is typically aerogenous in origin and tends to concentrate first in the apical lobe, progresses to the left cardiac lobe, and then ventrally to the additional lung field. Once the stethoscope takes the recorded sound, this data is then transferred to the computer 16 in accordance with known data transfer techniques. Preferably, the recorded sound taken by the stethoscope is a .wav file. Once the data is loaded and stored in the database 22, the analysis software 20 performs certain manipulations of the data in order to generate a number corresponding to a calculated lung score 70 as discussed below.

In accordance with the present invention as mentioned in the Summary, an algorithm is applied to the data within the .wav file in the form of a short-time Fourier transform that is performed on the raw data with a window size of approximately 512 data points and an approximate overlap of 50%. A Hamming function can be used as the windowing function. As discussed below with respect to FIGS. 3-7, the resulting data from each transform is plotted to form data points for a spectrogram that may be viewed by the user.

From various investigations, it has been determined that amplitudes of frequencies between 500-900 Hz represent those data points that can be numerically manipulated within an algorithm to indicate various levels of disease within an animal. As mentioned above, the data can be split into ten basic sets or bands, namely, amplitudes from 500-540 Hz, 540-580 Hz, 580-620 Hz, 620-660 Hz, 660-700 Hz, 700-740 Hz, 740-780 Hz, 780-820 Hz, 820-860 Hz, and 860-900 Hz. Calculations are made to then determine the calculated lung scores 70. The resulting scores are compared to established baseline data 74 that indicate some level of disease within the animal. As also mentioned in the Summary, Scaled Lung Scores can be used that correspond to ranges of the calculated lung scores to assign diagnoses for the level of disease within the animal. Recommended treatments may then be established based on the diagnoses. The diagnoses and treatments may also be stored in the database 22 wherein the diagnoses may be listings of particular lung ailments, and the treatments may include descriptions of various medications to be administered to the sick animal.

A perfectly healthy animal will ideally have little or no sound generated within the targeted frequency range and, therefore, a calculated score of 0 or a value much less than 75 would be calculated. Variation of lung sounds in normal cattle does occur and these variations are subject to a number of factors to include biological variation, digestive function, and immune status. Accordingly, it is also contemplated that the specific lung scores assigned to the various diagnoses can be shifted to account for any systemic variations that may occur in a group of animals. For calculated lung scores of approximately 150, the diagnosis will be low mild acute (Scaled Lung Score 3), indicating the presence of edema and exudates accompanied by reduced airflow through still functional tissue. These changes are very dynamic and have the potential to quickly become more severe in the absence of therapy and conversely, the animal's condition could dramatically improve in the presence of appropriate therapy. For calculated lung scores that occur between 0 and 149, there is considerable discretion by the caregiver to determine whether the animal has respiratory disease of any concern. Other factors may be analyzed, to include whether the animal has other signs of disease such as a temperature, depression, nasal discharge, etc. For calculated lung scores that reach 181, again through testing, it has been shown that these animals certainly have a level of respiratory disease that should be treated. Accordingly, at 181, the severe acute diagnosis is made which further indicates severe inflammatory responses including edema, effusion, and early consolidation in airways and alveolar spaces that is drastically reducing the efficiency of respiration. These cases deserve aggressive therapy, supportive care, and are at greater risk to require further therapy. For calculated lung scores that may fall between 150 and 181, the caregiver has a certain amount of discretion in determining the actual disease in the animal, and further evaluation of the animal can take place to confirm the nature of the disease. For calculated scores that reach 320, a chronic diagnosis can be made and some amount of nonfunctional lung tissue is typically involved in irreversible consolidation, coagulative necrosis, and possible abscess formation. For calculated lung scores falling between 181 and 320, again the caregiver has certain discretion in determining the actual nature of the respiratory disease occurring within the animal. For calculated scores above 320, it has been shown through testing that these animals have suffered some degree of irreversible loss of respiratory function that will decrease performance potential. Therapies depend on the percentage of lung involved, and the therapies are aimed at salvaging normal tissue and reducing abscess formation. Optimum treatment response and prudent antibiotic use depends on matching lung pathology associated with particular lung scores with pharmokinetics of antibiotics and ancillary drugs generated by a dynamic data base.

Now referring to FIG. 3, an example spectrogram 40 is illustrated which corresponds to a spectrogram that may be viewed by the user on the monitor 24 as a result of the analysis software 20 generating the spectrogram based upon data gathered from various observations. In this Figure, the spectrogram 40 includes data plotted as a function of the frequency of the sounds 42 over a period of time 44. More specifically, the frequencies are plotted in increments of 250 Hz, and sound is plotted over seconds. As shown in this Figure, the data points 46 show that there is only one occurrence of a sound that is above 500 Hz, therefore indicating a generally healthy animal. In this example, after application of the mathematical operations/algorithms, the diagnosis would in fact be normal. At the 0.80-second data point there is a single spike 47 that is greater than 500 Hz; however, this particular data point may be attributed to noise, such as background noise or even perhaps the heartbeat of the animal. Since this one data point is not repetitive over time, this data point can be ignored. In any event, even when this single data point is included in the data manipulated by the mathematical operations/algorithms, the lung score would still be near zero, therefore indicating very little lung pathology. The trimming function described above can remove much of the irrelevant background or environmental noise, such as pops or clicks generated from the stethoscope. A heart beat filter can reduce any existing heart beat noise, and constant noise at a particular frequency can also be removed using the noise filter. As mentioned, it is preferable to apply selected filters to eliminate as much noise as possible, such as background noise created by a heartbeat. This spectrogram may also be illustrated in color where volumes of the plotted frequencies correspond to particular colors.

Referring to FIG. 4, another spectrogram 40 is illustrated in which the amplitudes of the frequencies include a few data points 48 that fall between 500 and 900 Hz. After application of the mathematical operations/algorithms, this spectrogram is exemplary of one that could indicate a mild acute diagnosis. Since a caregiver does not have to make a diagnosis by merely looking at the spectrogram, the degree of subjectivity in making the diagnosis is greatly reduced therefore resulting in much more accurate diagnoses based on recorded data.

Referring to FIG. 5, the recorded sound shown in the spectrogram 40 is an example of one resulting in a severe acute diagnosis after application of the mathematical operations/algorithms. As shown, a number of additional data points 50 in this spectrogram fall between 500 and 900 Hz as compared to the data points 48 in the spectrogram of FIG. 4.

Referring to FIG. 6, yet another spectrogram 40 is shown illustrating a situation in which a chronic diagnosis can be made as reflected in the marked increase in the amplitude of the upper frequencies. As shown, there are many data points 54 that occur above 500 Hz that for each breath of the animal. After application of the mathematical operations/algorithms, this spectrogram indeed would result in a lung score corresponding to the chronic diagnosis.

As mentioned, in order to provide the most reliable sets of data to include the capability of visually displaying data in the form of spectrograms, it may be necessary to apply certain filters to the gathered data to eliminate various sources of noise. As mentioned, filtering techniques may be used to improve analytical data. These filters may include a heartbeat reduction filter, a pop/crackle filter, and a noise filter. All three filters will be based on an adaptive threshold piecewise interpolation technique. The heart beat filter will be focused on detecting periodic high amplitudes in the 0-250 Hz frequency range. The pop/crackle filter will be focused on periodic extremely high amplitudes in the 500-2000 Hz range. The noise filter will be focused on continuous high amplitudes in the 500-1000 Hz range. Whenever a section is detected by any of the filters, it is removed. The missing data is filled in by a linear interpolation. Unlike the collection of human sounds that may require a large bank of microphones to collect sound, assuming the electronic stethoscope is properly placed; diagnosis and treatments with the present invention can be accurately predicted by use of a single stethoscope. The Fourier transform brings the collected data into the frequency domain, thereby allowing the analysis software to determine which frequencies are contained in the sound and at which volume those frequencies exist. In general, the louder the sound at the frequencies of interest (500-900 Hz), the higher the lung score for the animal.

While the data obtained in the present invention can be an accurate predictor of the health of bovine species, the technique described herein would provide no useful diagnosis for humans. Human respiratory disease is typically far less severe than that of bovines, and the particular volumes and frequencies in humans would be much smaller over a long period of time. Human respiratory diseases are often signified by specific types of wheezes and crackles that have very specific lengths, volumes and frequency levels, none of which correspond to a similar diagnosis for bovine species.

Figure 7:
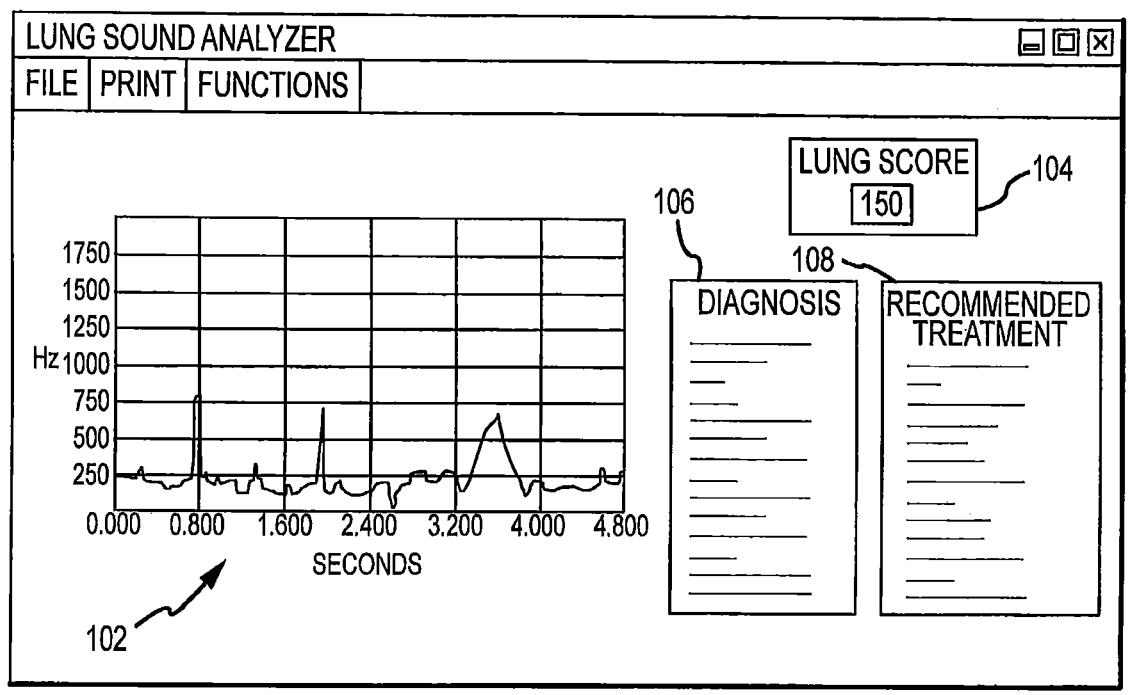
FIG. 7 is an example user interface screen showing a spectrogram, the calculated lung score corresponding to the spectrogram, a diagnosis, and one or more recommended treatments.

FIG. 7 is an example user interface screen 100 that includes a spectrogram 102, along with a corresponding display of the calculated lung score 104, a diagnoses 106, and a recommended treatment 108. In lieu of the calculated lung score, the Scaled Lung Score could be displayed on the screen. As mentioned above, the lung score may correlate to a diagnosis as well as one or more recommended treatments.

Figure 8:
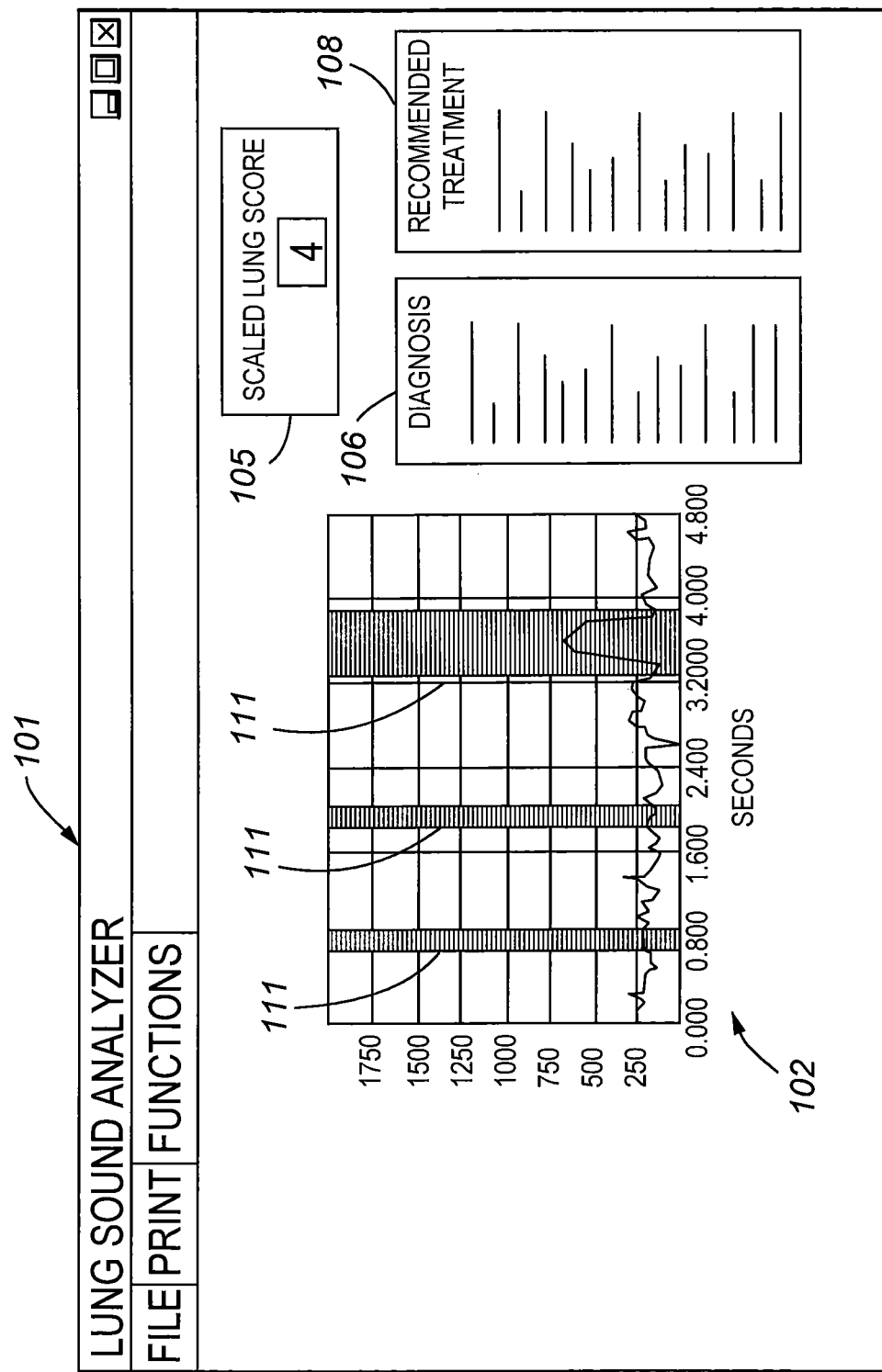
FIG. 8 is another example user interface screen showing the spectrogram of FIG. 7, wherein a user has trimmed frequencies that correspond to noise or other interfering frequencies not related to the targeted auscultated sounds of the animal.

FIG. 8 is another example user interface screen 101 that includes the spectrogram 102 of FIG. 7, a Scaled Lung Score 105, a diagnosis 106, and the recommended treatment 108. This screen 101 also shows those portions 111 of the spectrogram that the user has highlighted for removal as data that is not accurate in terms of the actual lung sounds. The portions 111 to be removed are noise or other interfering frequencies not related to the actual auscultated sounds of the animal. These interfering frequencies are identified as peaks in the spectrogram with amplitudes that are clearly out of range as compared to the remaining portions of the spectrogram. As mentioned, these interfering frequencies can be attributed to factors such as noise from the stethoscope, the heartbeat of the animal, etc. Once these areas have been trimmed, the user may again view the modified spectrogram to ensure the data appears accurate.

Other factors may also be considered when generating automatic diagnosis and treatments, such as other symptoms of the animal being analyzed. Therefore, it is also contemplated with the present invention that the automatic diagnoses and treatments can be further modified by analyzing other data such as the rectal temperature, projected market date, and risk category.

Figure 9A:
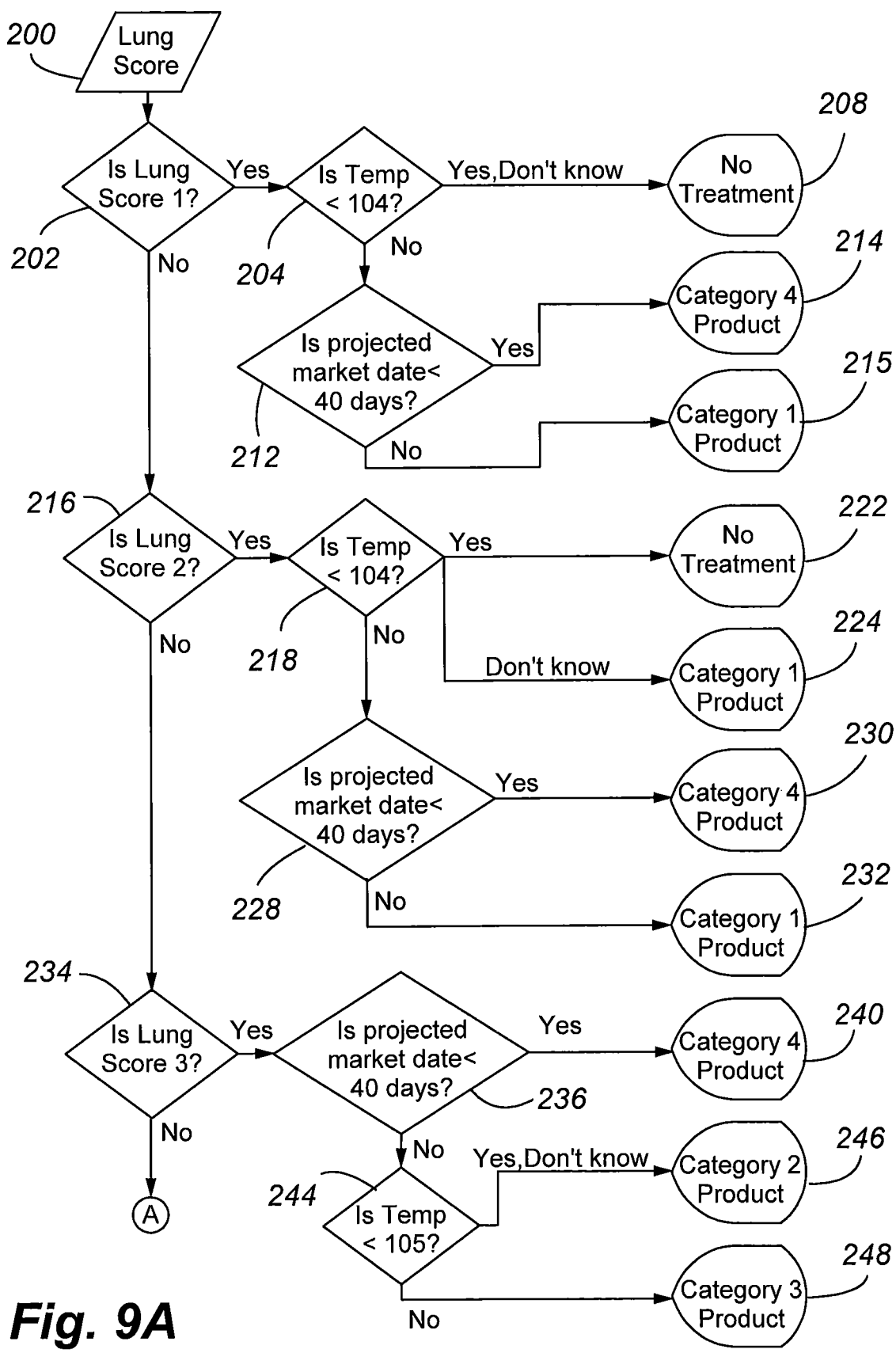
FIGS. 9A and 9B illustrate a flow diagram of a dynamic treatment matrix that provides a recommended treatment based upon consideration of a number of factors to include lung scores.
Figure 9B:
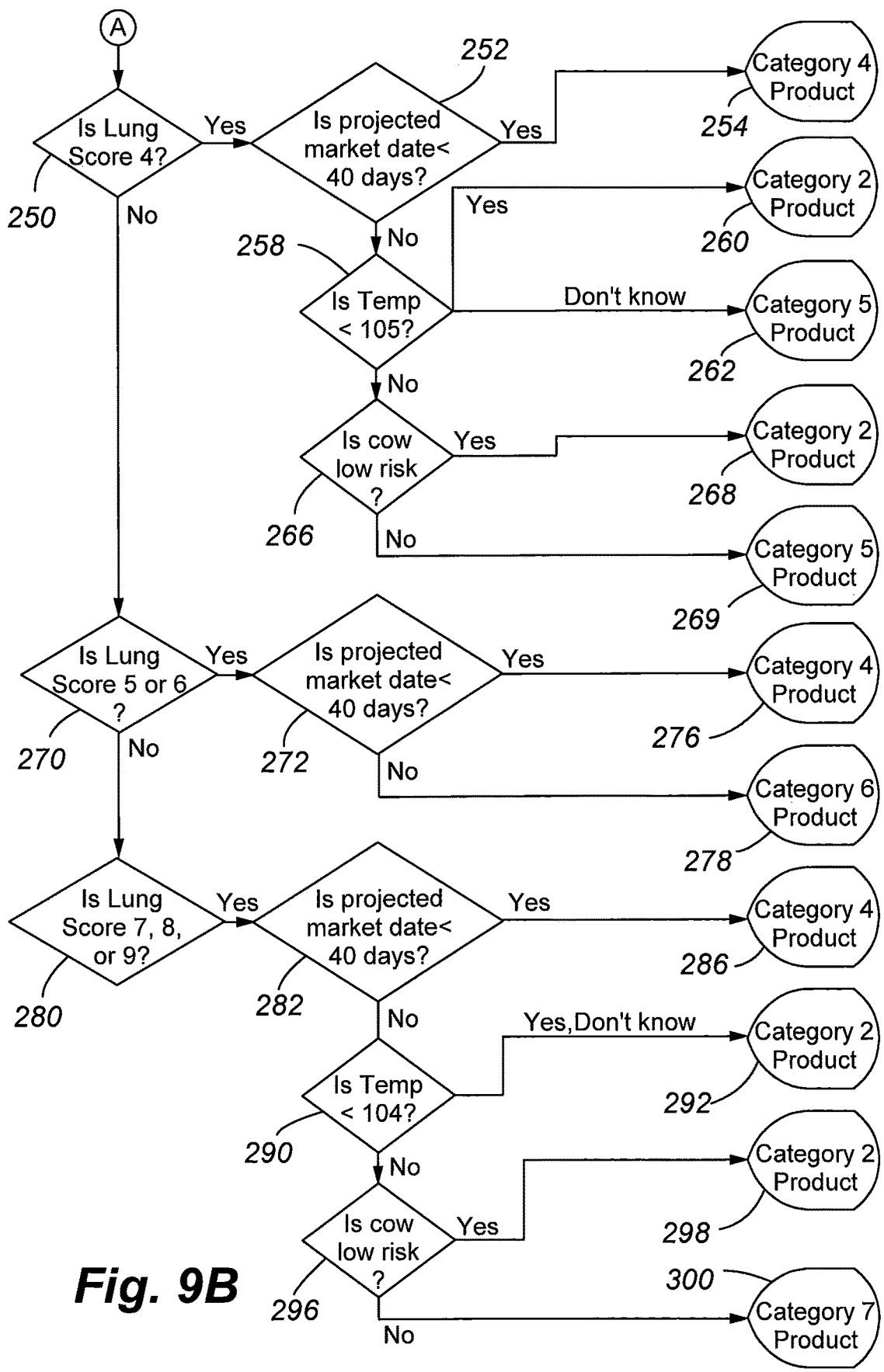

Referring to FIGS. 9A and 9B, a flowchart is provided for determining an appropriate treatment based upon a combination of these factors. The flowchart of FIGS. 9A and 9B may also be referred to as a dynamic treatment matrix that takes into consideration the various factors to determine an appropriate treatment. It shall be understood that in accordance with the method of the present invention, the only requirement for determining a recommended treatment is the determination of a lung score. The rest of the factors included within the dynamic treatment matrix are optional, but may provide a caregiver with additional treatment options if the other factors combine in a manner that may suggest an additional or perhaps a modified treatment.

In the recommended treatments within the matrix, the current pharmaceuticals are assigned a set of attributes that match designated lung scores. For example, one particular drug could work well on mild acute lung scores. Given that drugs change quite frequently, the current available drugs are stored in a database that is continually updated, ensuring that each drug is assigned the appropriate characteristics or case definition as set forth in the determination of the lung scores. Initially, the treatment recommended derives primarily from the lung score. In order to further consider the best match of the drug to be prescribed, the pharmaceuticals can also be assigned a set of attributes that match secondary considerations, such as whether the drug has shown good results for cattle having high rectal temperatures or good results for low risk cattle.

It is also contemplated with the present invention that historical data can be maintained for past treatment recommendations based upon the lung scores or other factors considered at the time. The historical analysis will include an evaluation of how successful treatment was, and the rate of treatment success can then be balanced against the treatment provided to alter or shift a recommended treatment.

The recommended treatments in FIGS. 9A and 9B are recommended administrations of various drug categories. The categories are defined as follows: Category 1 are low cost, broad spectrum antibiotics; Category 2 are low cost, broad spectrum antibiotics with a slightly broader spectrum capability; Category 3 are broad spectrum antibiotics aimed at log growth phase; Category 4 are broad spectrum antibiotics with withdrawal times less than forty days; Category 5 are broad spectrum antibiotics aimed at log growth phase with the addition of RNA synthesis inhibitors with an affinity for lung tissue; Category 6 are state-of-the-art, broadest spectrum antibiotics; and Category 7 are broadest spectrum antibiotics with highest affinity for consolidated lung tissue.

With respect to the risk levels recited as factors in FIGS. 9A and 9B, the following definitions apply: 1. High risk cattle are those that are any of the following: freshly weaned, co-mingled (purchased one or two at a time from many herds), auction market cattle (i.e. sold at a livestock yard), or an absence of vaccination history and 2. Low risk cattle are those cattle that do not meet any of the criteria for high risk.

Referring now to the flowchart beginning at FIG. 9A, at Block 200, the lung score is determined. At Block 202, if the Scaled Lung Score is 1, then at Block 204 the next determination is whether the temperature of the animal is below 104° F. The rectal temperature is used as the baseline temperature for this flowchart. If the temperature is less than 104° F., then at Block 208, the recommendation is no treatment. If the temperature is greater than 104° F., then at Block 212, the next determination is whether the projected market date is less than 40 days. If the projected market date is less than 40 days, then the treatment recommended at Block 214 is a Category 4 product. If the projected market date is not less than 40 days, then the recommended treatment at Block 215 is administration of the Category 1 product.

Referring to Block 216, if the Scaled Lung Score is 2, the next determination at Block 218 is whether the temperature is less than 104° F. If the temperature is less than 104° F., then the recommended treatment at Block 222 is no treatment. If the temperature is not known at Block 218, then the recommended treatment at Block 224 is administration of a Category 1 product. If the temperature is not less than 104° F., then the next determination is the projected market date at Block 228. If the projected market date is less than 40 days, then the recommended treatment is administration of a Category 4 product at Block 230. If the projected market date is not less than 40 days, then the recommended treatment is a Category 1 product at Block 232.

Referring to Block 234, if the Scaled Lung Score is 3, the next determination is whether the projected market date is less than 40 days at Block 236. If the projected market date is less than 40 days, then the recommended treatment is a Category 4 product at Block 240. If the projected market date is not less than 40 days, then the determination is made if the temperature is less than 105° F. at Block 244. If the temperature is less than 105° F., or if the temperature is not known, then the recommended treatment is administration of a Category 2 product at Block 246. If the temperature is not less than 105° F., then the recommended treatment at Block 248 is administration of a Category 3 product.

Referring to Block 250, if the Scaled Lung Score is 4, then the next determination is whether the projected market date is less than 40 days at Block 252. If the projected market date is less than 40 days, then the recommended treatment is administration of a Category 4 product at Block 254. If the projected market date is not less than 40 days, then at Block 258 a determination is made whether the temperature is less than 105° F. If the temperature is less than 105° F., then the recommended treatment is administration of a Category 2 product at Block 260. If the user does not know the rectal temperature, then the recommended treatment at Block 262 is administration of a Category 5 product at Block 262. If the temperature is not less than 105° F., then the next determination is made at Block 266 whether the animal is categorized as low risk. If the animal falls within the low risk category, then the recommended treatment is administration of a Category 2 product at Block 268. If the risk category is not low, then the recommended treatment is administration of a Category 5 product at Block 269.

Referring to Block 270, if the Scaled Lung Score is a 5 or 6, then the determination at Block 272 is whether the projected market date is less than 40 days. If the projected market date is less than 40 days, then the recommended treatment at Block 276 is administration of a Category 4 product. If the projected market date is not less than 40 days, then the recommended treatment at Block 278 is the administration of a Category 6 product.

Referring to Block 280, if the Scaled Lung Score is a 7, 8 or 9, then the determination at Block 282 is whether the projected market date is less than 40 days. If the projected market date is less than 40 days, then the recommended treatment is administration of a Category 4 product at Block 286. If the projected market date is not less than 40 days, then the next determination at Block 290 is whether the temperature is less than 104° F. If the temperature is less than 104° F. or if the temperature is unknown, then the recommended treatment is administration of a Category 2 product at Block 292. If the temperature is not less than 104°

F., then the next determination is whether the animal is low risk at Block 296. If the risk factor is low, then the recommended treatment at Block 298 is administration of a Category 2 product. If the risk factor is not low, then the recommended treatment is administration of a Category 7 product at Block 300.

Figure 10:
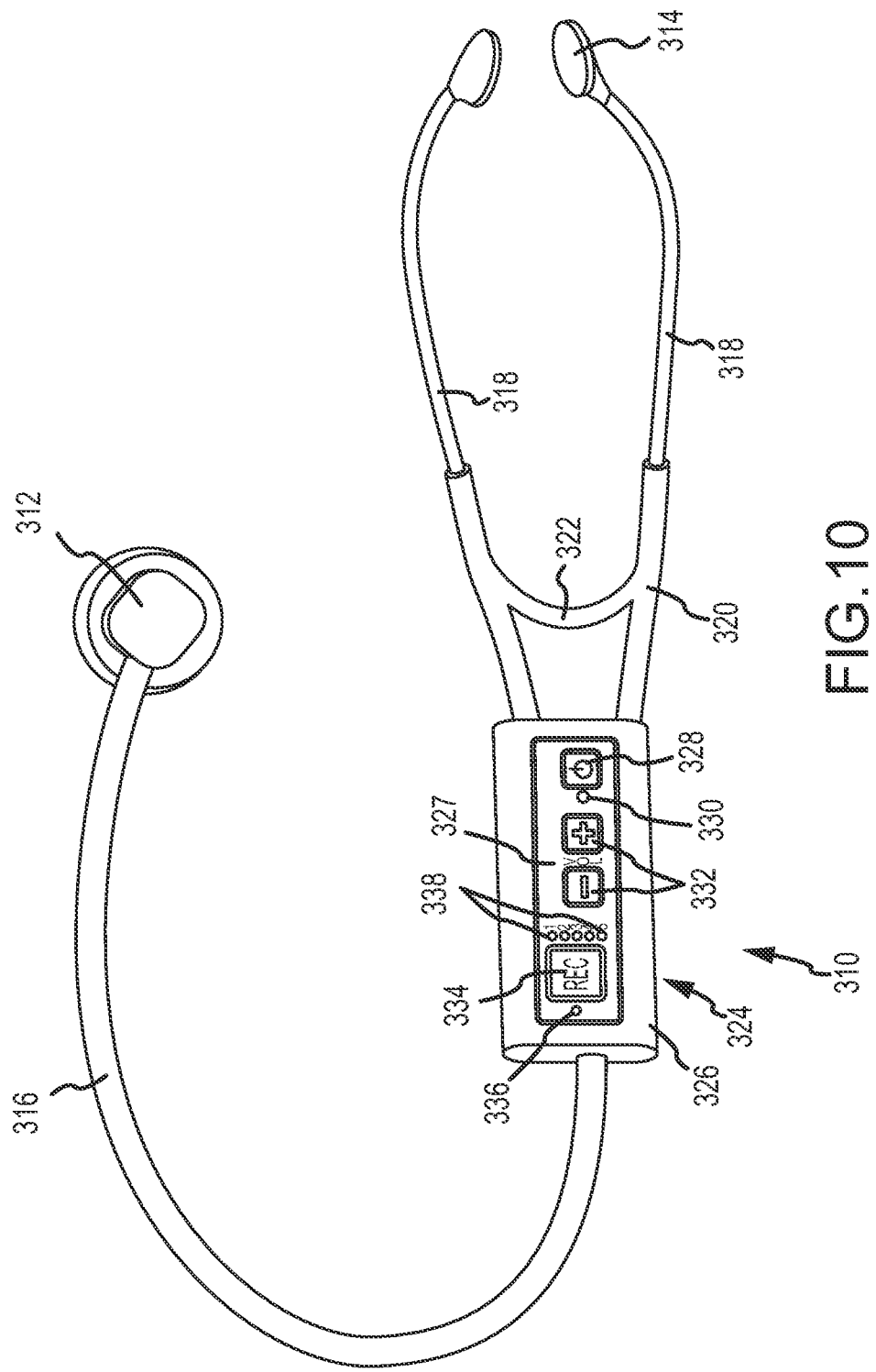
FIG. 10 is a plan view of another embodiment of the present invention, namely, an electronic digital stethoscope with an integral display.

FIG. 10 shows another preferred embodiment of the present invention, namely, a digital stethoscope 310 with an integrated recording and display unit 324. The stethoscope 310 may include a standard construction as shown including a chest piece 312 and ear pieces 314. Sounds are detected by the chest piece 312 and are transferred to the integrated recording and display unit 324. A communication cord 316 interconnects the chest piece to the unit 324. Listening extensions 318 interconnect the ear pieces to the unit 324. Optionally, additional support can be provided to the extensions 318 by support sleeves 320 and a support bridge 322. One example of a construction for a digital electronic stethoscope that can be used with the present invention includes a line of commercially available electronic stethoscopes sold and manufactured by 3M® known as the Littmann® electronic stethoscopes. These devices may be modified to incorporate the special functionality of the present invention to include the integrated unit 324.

Referring to the unit 324, it includes a housing 326 which houses the electronic components of the stethoscope. Mounted on one side of the housing 326 is a display panel 327. On the display panel are a number of features to include an on/off button 328, an on/off light indicator 330, volume control buttons 332, a record button 334 and a record indication light 336. In order to power up the stethoscope, the user depresses the on/off button 328, and the on/off light indicator 330 will illuminate when the device is powered. The device 310 may be powered by batteries and/or by a conventional AC power source in which the device 310 may have a detachable power cord (not shown) for selectively powering the unit with the AC power source.

When the user wishes to record a sound, the user places the chest piece 312 at the desired location on the animal, and the user then depresses the record button 334 to initiate recording of sounds. The record indicator light 336 will illuminate to indicate to the user that the device is recording and/or that the sounds have been successfully recorded and have been transmitted to a remote computer that will manipulate the digital sound data for producing a tangible user output. The user depresses the record button 334 again in order to terminate the recording and to establish a recorded sound record for manipulation by the software/firmware to generate the lung score or other health indication output. Alternatively, the device can be set to record for a pre-determined time period requiring the use to only press the record button once.

Figure 11:
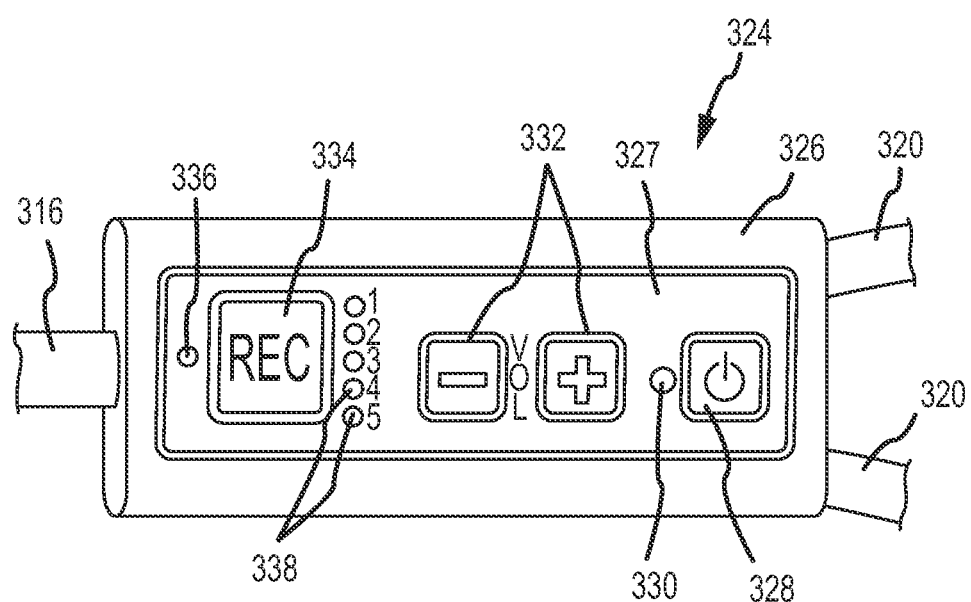
FIG. 11 is an enlarged plan view of the integral display of the device of FIG. 10.

Also located on the display panel 327 is a health status indicator in the form of a plurality of health indicator lights 338. These indicator lights may represent a lung score, or may represent some other indication as to the health of the animal. As best seen in FIG. 11, in one embodiment of the present invention, the health indicator lights 338 are numbered 1-5. The illumination of one of the lights or a group of lights indicate a lung score or some other health status for the animal. For example, light number one, if illuminated, could indicate a normal condition for the animal. Light number two, if illuminated, could indicate a mild, acute condition. Light number three, if illuminated, could indicate a moderate acute condition. Light number four, if illuminated, could indicate a severe acute condition, and light number five, if illuminated, could indicate a chronic condition.

If it is desired to record lung sounds again, the user would simply depress the record button again and the system software automatically creates another data record. If the user wishes to cancel a recording or to otherwise delete a recording, the user can be provided this option on a user dialogue display (not shown) that can also be incorporated on the display panel 327. A user dialogue display is explained below with respect to the embodiment of FIG. 13.

In another aspect of the invention, it is also contemplated that the system software could incorporate controls such that recorded lung sounds were not processed unless the recorded sounds met pre-designated criteria to ensure the recorded sounds did not have excess environmental noise. Although filters can be used to separate and remove noise, it is advantageous for the recorded sound to be as "clean" as possible so that there are enough data points in the selected frequencies to ensure the algorithm(s) can be applied without appreciable output errors. Therefore, the user display may also incorporate one or more additional indicator lights, or may provide a particular light pattern or color scheme for the indicator lights 338 indicating that a "clean" lung sound can be recorded based on a screening of the lung sound as it is initially recorded. This screening of the recorded lung sound as it is first recorded can also be referred to as a "test" sound. In addition to environmental noise, poor sound recordation can be attributed to misplacement of the device such that the amplitude of sound recorded is not adequate for processing. Pre-determined parameters can be developed and used in the software for expected frequency ranges and amplitudes for a typical "clean" sound.

In addition to a numbering sequence for indicator lights 338, other types of visual indicators could be provided to indicate the health of the animal, such as additional lights, or a text message on a user/dialogue display in which a condition of the animal would appear in an explanatory message with the detected condition.

One can appreciate the advantages of having the status of the animal displayed directly on the digital stethoscope. The user avoids having to view another device in order to obtain the lung score/health status of the animal. The user can conduct repeated sound gathering operations in order to confirm consistency among the outputs provided by the indicator lights/dialogue displays over a short time period. Thus, a user can quickly gather data sets and can immediately visually confirm consistency among the data sets directly on the stethoscopic device.

In terms of how the indicator lights are illuminated, processing of the recorded lung sound data can be done either by a remote computing device in which the stethoscope communicates wirelessly with the remote computing device, or the digital stethoscope itself may have an integral processor having the capability to process the lung sound data and to generate lung scores or other outputs indicating the health of the animal based upon the auscultation analysis.

Referring to FIG. 12, in another embodiment of the invention, a system is provided for gathering data on animals in which the digital stethoscope 310 is one of the field devices used within the system. More specifically, FIG. 12 illustrates a number of field devices that communicate wirelessly with a remote computer 368, and the data may then be recorded and manipulated to generate desired outputs to a user. The system contemplates a number of different field devices to include an RFID reader 350 for identifying and tracking the animal being examined, a scale head 352 that records the weight of an animal on an associated scale (not shown), a diagnostic device 354 that may take other measurements or observations of the animal, and a temperature probe 356 for recording the temperature of the animal. Each of the field devices have a wireless capability, and may therefore communicate wirelessly with the remote computer 368. Accordingly, each of the field devices are illustrated with a wireless adaptor 360, and the field devices can be considered communication endpoints. The remote computing device 368 may include standard components to include the computer/processor 372, a user display 370 and input devices 374 such as a keyboard and mouse. The remote computing device could also be a server. One or more gateway devices 362 such as wireless access points or switches can be used to ensure full wireless coverage of the area in which the field devices are located. From the gateway device(s) 362, the data recorded by the field devices is transmitted through a communications network 366 such as the Internet, an intranet, a LAN, etc. Once the data is received by the remote computer 368, manipulation of the digitized sound data takes place in order to generate outputs in the form of visual displays, reports, or others for the user. The data from the other field devices may also be considered in the algorithm(s) to supplement reporting and may also be used to generate a recommended treatment in which data from the other field devices is used in yet another group of algorithms or formulas relating to the generation of recommended treatments.

The outputs generated regarding a diagnosis and treatment are communicated to selected user(s) back through the communications network 366. These outputs can be sent back to the user(s) of the field devices, or to other users who may have, for example, personal digital assistants 364. Therefore, it is contemplated with the FIG. 12 that comprehensive data may be transmitted simultaneously to the remote computer 368, data manipulations take place and then tangible outputs are made available for immediate use by a user. In one aspect of this embodiment, once the digital stethoscope 310 is activated, the digital stethoscope may query the presence of other field devices that may have recorded data on the same animal being examined. This query can then trigger a wireless command, either from the digital stethoscope or from the remote computer 368, for the field devices to commence transmitting selected data for the animal being examined. Therefore, from a review of FIG. 12 it is apparent that for a wireless communication system, a user can be provided a tremendous amount of valuable information regarding the animal being treated.

Figure 13:
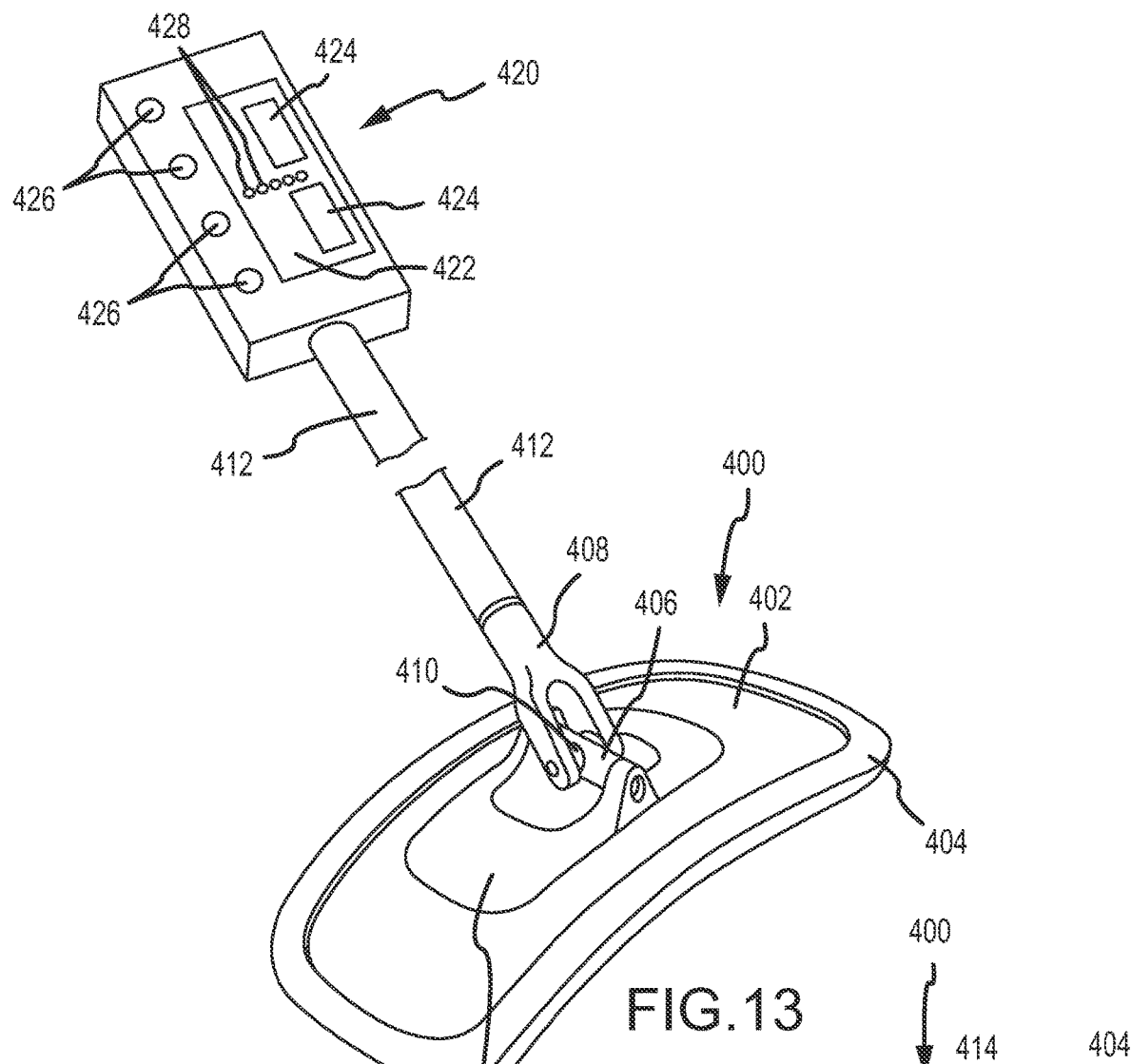
FIG. 13 is a fragmentary top perspective view of a wireless audio digital recording unit in accordance with another embodiment of the present invention.
Figure 14:
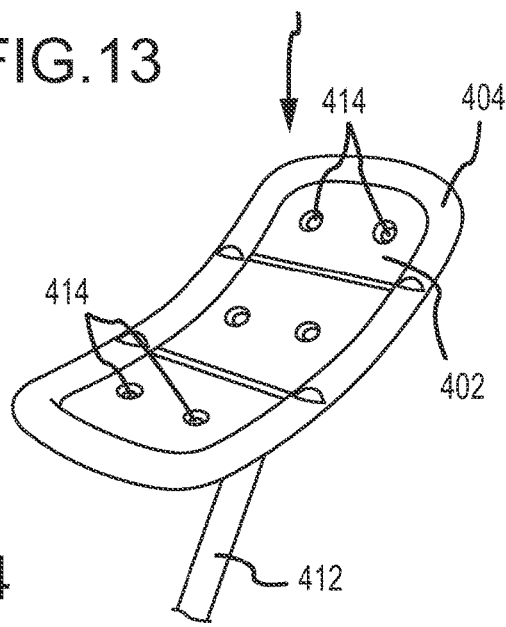
FIG. 14 is a reverse perspective view of the device shown in FIG. 13.

In yet another embodiment of the present invention, referring to FIGS. 13 and 14, another type of sound gathering device is illustrated. More specifically, FIGS. 13 and 14 illustrate a wireless audio digital recording unit 400 that is capable of obtaining lung sounds, and then transmitting the information wirelessly to the remote computer 368, or the device 400 may have its own microprocessor, memory, software/firmware, and database(s) for manipulation of the data recorded to generate a tangible output for the user.

More specifically, the unit 400 includes a paddle 402 that houses the sensors (not shown) for recording sounds. The paddle 402, as shown, may have a curvature in order that the paddle may be conveniently placed at a targeted location on the animal to best capture sounds. A peripheral pad or protective member 404 is also illustrated to protect the paddle 402 and to assist the user in holding the paddle on the animal. The paddle is rotatably mounted to an extension pole 412. As shown, the rotatable connection can be achieved by a transverse mounting rod 406 secured to a base member 407. The distal end of the pole 412 may include a yoke 408 that is attached to the mounting rod 406 by pin 410. Thus, the paddle 402 may be rotatable in a first axis about the pin 410, and rotatable about the mounting rod 406 in another axis oriented orthogonal to the first axis. Referring to FIG. 14, sensor openings 414 are provided on the lower surface of the paddle 402 enabling the sensors (not shown) to record sounds. A sensor may include one or more multi channel microphones incorporated therein for detecting and transmitting auscultated sounds to the microprocessor.

In another aspect of the invention as shown in FIG. 13, it is also contemplated that that device 400 may optionally have its own integral electronic control and display unit 420. This unit 420 may include various control buttons 426, similar to those on the device of FIG. 10. Additionally, the unit 420 may include a display panel 422 with one or more user interface displays/dialogue displays 424. These displays are capable of displaying to the user the particular health status of the animal as the data has been manipulated through one or more algorithms in the unit 420 that has its own integral microprocessor, memory, software/firmware, and database(s). Additionally, the FIG. 13 illustrates a number of display lights 428 which may also be used to indicate the health status of the animal, and the function of these lights may be in accordance with what is described with respect to the display lights 338 for the embodiment of FIG. 11.

Figure 15:
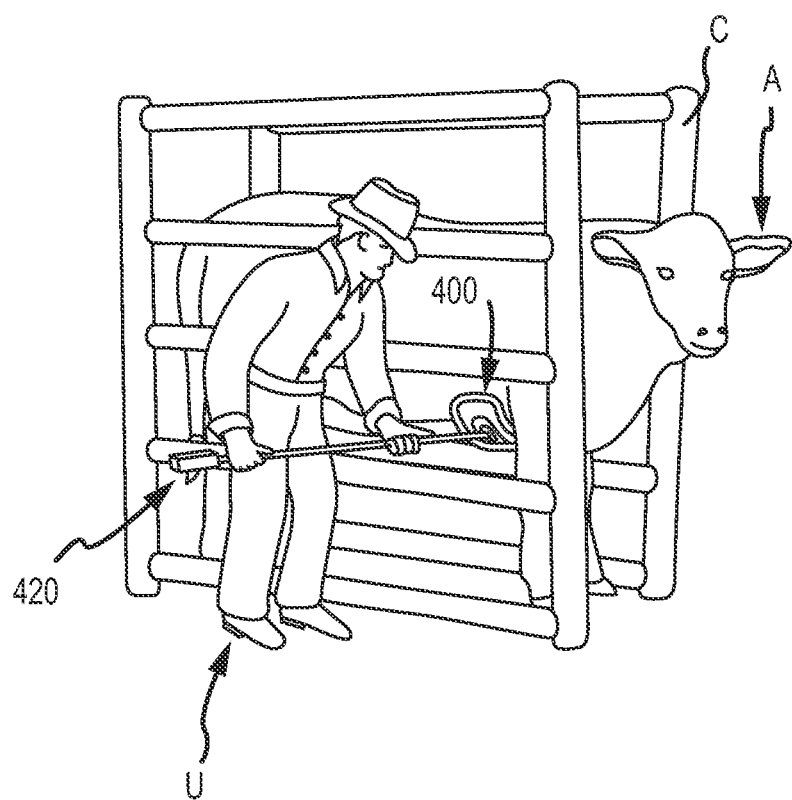
FIG. 15 illustrates use of the device of FIG. 13, for example, to obtain lung sounds from an animal in a livestock chute.

Referring to FIG. 15, a user U places the device 400 at the desired location on the animal A for recording lung sounds. As shown, the user U is able to record the lung sounds without having to place the hands or arms within the cage C. Therefore, this provides a much safer manner for user to obtain sounds from the animal. The device 400 may also have a wireless capability in order to transmit and receive signals from a remote computer as described above with respect to the embodiments of FIGS. 10-12. Therefore, the device 400 can also be an additional field device within the system of FIG. 12.

There are a number of advantages associated with the embodiments illustrated in FIGS. 10-14. One distinct advantage provided is the capability for a user to visually observe the health status of an animal in real time at the location where data is gathered, without having to later view another diagnostic device and perhaps at another location. Additionally, in accordance with the system of FIG. 12, comprehensive data can be obtained regarding the health status of an animal for generating detailed reports, or to otherwise analyze recorded data for purposes of diagnosing the health of the animal and for generating treatment options.

Although the present invention has been set forth with respect to one or more preferred embodiments, it shall be understood that various other changes and modifications can be made to the invention in accordance with the scope of the claims appended hereto.

What is claimed is:

1. An electronic digital stethoscope especially adapted for auscultation analysis of lungs sounds of a non-human animal, comprising:
   a chest piece;
   at least one earpiece;
   a housing connected to said chest piece and said at least one earpiece, said housing comprising an integrated recording and display unit, said unit including (i) a processor in said housing for processing digital sound data of the lungs sounds of the non-human animal received by auscultation, (ii) computer coded instructions for manipulating the digital sound data through incorporation of at least one numerical algorithm that calculates at least one numerical value, said numerical algorithm utilizing selected frequencies of auscultated lung sounds of the non-human animal, said numerical algorithm generating a first set of data including the at least one numerical value, corresponding to an indication of a health state of the non-human animal;

wherein said at least one numerical value is calculated by said processor by use of a Fourier transform performed on said digital sound data, plotting resulting data from said Fourier transform in a frequency domain wherein amplitudes of frequencies between about 500-900 HZ differentiate between categories of sounds corresponding to various levels of respiratory disease;

wherein the at least one numerical value is a calculated numerical lung score compared to threshold values that correspond to respiratory conditions indicating the health status wherein said calculated numerical lung score is compared to a threshold value that corresponds to a respiratory condition expressed in a scaled lung score;

wherein a health status indicator in said housing including at least one of a plurality of health indicator lights that indicate the health status of the non-human animal;

wherein said health indicator lights include a plurality of lights that correspond to a health condition of said animal derived from said scaled lung score including a mild condition, a mild acute condition, a moderate acute condition, a severe acute condition, and a chronic condition.

2. The electronic digital stethoscope, as claimed in claim 1, wherein: said plurality of health indicator lights of said health status indicator includes at least one numbered illuminated light that, when illuminated, corresponds to the health status, said health status including at least one of a normal condition, a mild acute condition, a moderate acute condition, a severe acute condition, or a chronic condition.

3. The electronic digital stethoscope, as claimed in claim 1, wherein: said plurality of health indicator lights of said health status indicator include five numbered health indicator lights that when illuminated, indicate five corresponding health conditions.

4. The electronic digital stethoscope, as claimed in claim 3, wherein: said five corresponding health conditions include a normal condition, a mild acute condition, a moderate acute condition, a severe acute condition and a chronic condition.

5. An electronic digital stethoscope especially adapted for auscultation analysis of lungs sounds of a non-human animal, comprising:
a chest piece;
at least one earpiece;
a housing connected to said chest piece and said at least one earpiece, said housing comprising an integrated recording and display unit, said unit including (i) a processor in said housing for processing digital sound data of the lungs sounds of the non-human animal received by auscultation, (ii) computer coded instructions for manipulating the digital sound data through incorporation of at least one numerical algorithm that is used by said processor to calculate at least one numerical value, said numerical algorithm utilizing selected frequencies of auscultated lung sounds of the non-human animal, wherein said at least one numerical value calculated by said processor includes use of a Fourier transform performed on said digital sound data, plotting resulting data from said Fourier transform in a frequency domain wherein amplitudes of frequencies between about 500-900 HZ differentiate between categories of sounds corresponding to various levels of respiratory disease and said housing including a health status indicator and wherein said health status indicator provides a health status of the non-human animal based upon an auscultation analysis that has taken place with auscultated lung sounds recorded by the stethoscope upon the non-human animal;

wherein the at least one numerical value is a calculated numerical lung score compared to threshold values that correspond to respiratory conditions indicating the health status and wherein said calculated numerical lung score is compared to a threshold value that corresponds to a respiratory condition expressed in a scaled lung score;

wherein the health status is made observable to a user on said health status indicator that indicates the health status of the non-human animal wherein said health status indicator includes a plurality of lights that correspond to at least one of:

a health condition of said animal derived from said scaled lung score including a mild condition, a mild acute condition, a moderate acute condition, a severe acute condition, and a chronic condition.

6. A stethoscope, as claimed in claim 5, wherein:
said unit further includes a wireless adapter for wireless communication.

7. The electronic digital stethoscope, as claimed in claim 5, wherein
the health status indicator includes at least one numbered light that, when illuminated, corresponds to a health condition of the animal, said health condition including at least one of a normal condition, a mild acute condition, a moderate acute condition, a severe acute condition and a chronic condition.

8. An electronic digital stethoscope especially adapted for auscultation analysis of lungs sounds of a non-human animal, comprising:
a chest piece;
a housing connected to said chest piece, said housing comprising an integrated recording and display unit, said unit including (i) a processor in said housing for processing digital sound data of the lungs sounds of the non-human animal received by auscultation, (ii) computer coded instructions for manipulating the digital sound data through incorporation of at least one numerical algorithm that calculates at least one numerical value, said numerical algorithm utilizing selected frequencies of auscultated lung sounds of the non-human animal, and said housing including a health status indicator and wherein the at least one numerical value is calculated by said processor by use of a Fourier transform performed on said digital sound data, plotting resulting data from said Fourier transform in a frequency domain wherein amplitudes of frequencies between about 500-900 HZ differentiate between categories of sounds corresponding to various levels of respiratory disease;

wherein said health status indicator provides a health status of the non-human animal based upon an auscultation analysis that has taken place with auscultated lung sounds recorded by the stethoscope upon the non-human animal;

wherein the at least one numerical value is a calculated numerical lung score compared to threshold values that correspond to respiratory conditions indicating the health status;

wherein said calculated numerical lung score is compared to a threshold value that corresponds to a respiratory condition expressed in a scaled lung score;

wherein said health status indicator includes a plurality of lights that are either illuminated or not illuminated, wherein if the lights are illuminated, the lights indicate a health status and if not illuminated, the lights do not indicate a health status of the non-human animal; and wherein illuminated health lights correspond to:

a health condition of said animal derived from said scaled lung score including a mild condition, a mild acute condition, a moderate acute condition, a severe acute condition, and a chronic condition.

\* \* \* \* \*

UNITED STATES PATENT AND TRADEMARK OFFICE
CERTIFICATE OF CORRECTION

| | |
|---|---|
| PATENT NO. | : 11,389,080 B2 |
| APPLICATION NO. | : 13/442569 |
| DATED | : July 19, 2022 |
| INVENTOR(S) | : Randolph K. Geissler et al. |

It is certified that error appears in the above-identified patent and that said Letters Patent is hereby corrected as shown below:

In the Claims

Column 19 Line 49 to Column 20 Line 28, Claim 5 should read:
5. An electronic digital stethoscope especially adapted for auscultation analysis of lungs sounds of a non-human animal, comprising: a chest piece; at least one earpiece; a housing connected to said chest piece and said at least one earpiece, said housing comprising an integrated recording and display unit, said unit including (i) a processor in said housing for processing digital sound data of the lungs sounds of the non-human animal received by auscultation, (ii) computer coded instructions for manipulating the digital sound data through incorporation of at least one numerical algorithm that is used by said processor to calculate at least one numerical value, said numerical algorithm utilizing selected frequencies of auscultated lung sounds of the non-human animal, wherein said at least one numerical value calculated by said processor includes use of a Fourier transform performed on said digital sound data, plotting resulting data from said Fourier transform in a frequency domain wherein amplitudes of frequencies between about 500-900 HZ differentiate between categories of sounds corresponding to various levels of respiratory disease and said housing including a health status indicator and wherein said health status indicator provides a health status of the non-human animal based upon an auscultation analysis that has taken place with auscultated lung sounds recorded by the stethoscope upon the non-human animal; wherein the at least one numerical value is a calculated numerical lung score compared to threshold values that correspond to respiratory conditions indicating the health status; wherein said calculated numerical lung score is compared to a threshold value that corresponds to a respiratory condition expressed in a scaled lung score; wherein the health status is made observable to a user on said health status indicator that indicates the health status of the non-human animal wherein said health status indicator includes a plurality of lights that correspond to a health condition of said animal derived from said scaled lung score including a mild condition, a mild acute condition, a moderate acute condition, a severe acute condition, and a chronic condition.

Signed and Sealed this
Thirtieth Day of August, 2022

Katherine Kelly Vidal
*Director of the United States Patent and Trademark Office*